(12) United States Patent
Jerome et al.

(10) Patent No.: US 6,495,346 B1
(45) Date of Patent: Dec. 17, 2002

(54) COMPLEX-FORMING PROTEINS

(75) Inventors: Valerie Jerome, Cölbe; Hans-Harald Sedlacek; Rolf Müller, both of Marburg, all of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/481,593

(22) Filed: Jan. 12, 2000

(30) Foreign Application Priority Data

Jan. 12, 1999 (DE) ......................................... 199 00 743

(51) Int. Cl.$^7$ ...................... C12N 15/62; A61K 38/20; C07K 14/54

(52) U.S. Cl. .................. 435/69.7; 435/69.5; 435/69.52; 424/85.1; 424/85.2; 536/23.4; 536/23.5; 536/23.51; 530/351

(58) Field of Search .......................... 435/6, 69.7, 69.5, 435/69.52; 536/23.4, 23.5; 530/351; 424/85.1, 85.2

(56) References Cited

U.S. PATENT DOCUMENTS

| | | | |
|---|---|---|---|
| 5,830,880 A | 11/1998 | Sedlacek et al. | 514/44 |
| 5,854,019 A | 12/1998 | Sedlacek et al. | 435/69.1 |
| 5,885,833 A | 3/1999 | Mueller et al. | 435/372 |
| 5,916,803 A | 6/1999 | Sedlacek et al. | 435/320.1 |
| 6,033,856 A | 3/2000 | Koerner et al. | 435/6 |
| 6,057,133 A * | 5/2000 | Bauer et al. | 435/69.7 |
| 6,110,698 A * | 8/2000 | Heinrich et al. | 435/29 |

FOREIGN PATENT DOCUMENTS

| | | |
|---|---|---|
| EP | 0 805 209 | 11/1997 |

OTHER PUBLICATIONS

Valerie Jerome et al., "Tissue–Specific, Cell Cycle–Regulated Chimeric Transcription Factors for the Targeting of Gene Expression to Tumor Cells.", Human Gene Therapy, vol. 9, No. 18, pp. 2653–2659, 1998, XP–000915434.

Yaolin Wang et al., "A regulatory system for use in gene transfer.", Proceedings of the National Academy of Science, vol. 91, pp. 8180–8184, 1994, XP–002121654.

Milan Chytil et al., "The orientation of the AP–1 heterodimer on DNA strongly affects transcriptional potency.", Proceedings of the National Academy of Science, vol. 95, pp. 14076–14081, 1998.

* cited by examiner

*Primary Examiner*—W. Gary Jones
*Assistant Examiner*—Arun Chakrabarti
(74) *Attorney, Agent, or Firm*—Heller Ehrman White and McAuliffe

(57) ABSTRACT

The invention relates to a complex of specifically complex-forming proteins which are not naturally occurring, comprising the following components: a) at least one ligand specific for a target structure, b) at least one protein comprising a mutated dimerization domain, the mutated dimerization domain having been derived by mutation of a naturally occurring dimerization domain, it being possible for this mutated dimerization domain to interact specifically with component c) and the component b) being connected covalently to the component a), c) at least one protein comprising a mutated dimerization domain, the mutated dimerization domain having been derived by mutation of a naturally occurring dimerization domain, it being possible for this mutated dimerization domain to interact specifically with component b) and the component c) is linked covalently to the component d), and d) at least one effector. In addition, the invention relates to the use and preparation of these complexes, and to nucleic acid constructs coding for the proteins mentioned and use thereof.

12 Claims, 7 Drawing Sheets

Figure 3

Activator subunit A

| Cyclin A promoter NS -214 to +100 | NLS (SV40) aa 126-132 | TAD (VP16) aa 411-455 | c-jun (mutated) aa 276-312 |

Activator subunit B

| Tyrosine promoter [NS -2014 to -1820]$_{2x}$ NS -209 to +51 | NLS (SV40) aa 126-132 | DB (Gal4) aa 1-147 | c-fos (mutated) aa 160-196 |

Figure 4

Mutations of c-jun (zipper)

Wild-type (wt)  RIARLEEKVKTLKAQNSELASTANMLREQVAQLKQKV (SEQ ID NO.: 22)
(aa 276-312)
                         ↓      ↓              ↓
Mutated (m)             (E)    (E)            (E)
                        283    288            302

Mutations of c-fos (zipper)

Wild-type (wt)  LTDTLQAETDQLEDEKSALQTEIANLLKEKEKLEFIL (SEQ ID NO.: 23)
(aa 160-196)
                        ↓     ↓      ↓
Mutated (m)            (K)   (K)    (K)
                       167   172    181

The activator-responsive promoter and the effector gene

SEQUENCE LISTING

<160> NUMBER OF SEQ ID NOS: 23

<210> SEQ ID NO 1
<211> LENGTH: 20
<212> TYPE: PRT
<213> ORGANISM: Unknown
<220> FEATURE:
<223> OTHER INFORMATION: Fusogenic peptide

<400> SEQUENCE: 1

Gly Leu Phe Glu Ala Leu Leu Glu Leu Leu Glu Ser Leu Trp Glu Leu
1               5                   10                  15

Leu Leu Glu Ala
            20

<210> SEQ ID NO 2
<211> LENGTH: 29
<212> TYPE: PRT
<213> ORGANISM: Unknown
<220> FEATURE:
<223> OTHER INFORMATION: Fusogenic peptide

<400> SEQUENCE: 2

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Cys
            20                  25

<210> SEQ ID NO 3
<211> LENGTH: 19
<212> TYPE: PRT
<213> ORGANISM: Unknown
<220> FEATURE:
<223> OTHER INFORMATION: Fusogenic peptide

<400> SEQUENCE: 3

Phe Ala Gly Val Val Leu Ala Gly Ala Ala Leu Gly Val Ala Ala Ala
1               5                   10                  15

Ala Gln Ile

<210> SEQ ID NO 4
<211> LENGTH: 20
<212> TYPE: PRT
<213> ORGANISM: Unknown
<220> FEATURE:
<223> OTHER INFORMATION: Fusogenic peptide

<400> SEQUENCE: 4

Gly Leu Phe Gly Ala Ile Ala Gly Phe Ile Glu Gly Gly Trp Trp Gly
1               5                   10                  15

Met Ile Asp Gly
            20

<210> SEQ ID NO 5
<211> LENGTH: 40
<212> TYPE: PRT
<213> ORGANISM: Unknown
<220> FEATURE:
<223> OTHER INFORMATION: Fusogenic peptide

<400> SEQUENCE: 5

Gly Leu Phe Gly Ala Ile Ala Gly Phe Ile Glu Asn Gly Trp Glu Gly
1               5                   10                  15

Met Ile Asp Gly Gly Leu Phe Gly Ala Ile Ala Gly Phe Ile Glu Asn
            20                  25                  30

Gly Trp Glu Gly Met Ile Asp Gly
            35                  40

<210> SEQ ID NO 6
<211> LENGTH: 11
<212> TYPE: PRT
<213> ORGANISM: Unknown
<220> FEATURE:
<223> OTHER INFORMATION: Fusogenic peptide

<400> SEQUENCE: 6

Gly Leu Phe Gly Ala Ile Ala Gly Phe Ile Glu
1               5                   10

<210> SEQ ID NO 7
<211> LENGTH: 11
<212> TYPE: PRT
<213> ORGANISM: Unknown
<220> FEATURE:
<223> OTHER INFORMATION: Fusogenic peptide

<400> SEQUENCE: 7

Ala Leu Phe Gly Ala Ile Ala Gly Phe Ile Glu
1               5                   10

<210> SEQ ID NO 8
<211> LENGTH: 11
<212> TYPE: PRT
<213> ORGANISM: Unknown
<220> FEATURE:
<223> OTHER INFORMATION: Fusogenic peptide

<400> SEQUENCE: 8

Leu Phe Leu Gly Ala Ile Ala Gly Phe Ile Glu
1               5                   10

<210> SEQ ID NO 9

```
<211> LENGTH: 11
<212> TYPE: PRT
<213> ORGANISM: Unknown
<220> FEATURE:
<223> OTHER INFORMATION: Fusogenic peptide

<400> SEQUENCE: 9

Leu Leu Leu Gly Ala Ile Ala Gly Phe Ile Glu
1               5                   10

<210> SEQ ID NO 10
<211> LENGTH: 11
<212> TYPE: PRT
<213> ORGANISM: Unknown
<220> FEATURE:
<223> OTHER INFORMATION: Fusogenic peptide

<400> SEQUENCE: 10

Leu Ile Leu Gly Ala Ile Ala Gly Phe Ile Glu
1               5                   10

<210> SEQ ID NO 11
<211> LENGTH: 11
<212> TYPE: PRT
<213> ORGANISM: Unknown
<220> FEATURE:
<223> OTHER INFORMATION: Fusogenic peptide

<400> SEQUENCE: 11

Gly Ile Phe Gly Ala Ile Ala Gly Phe Ile Glu
1               5                   10

<210> SEQ ID NO 12
<211> LENGTH: 11
<212> TYPE: PRT
<213> ORGANISM: Unknown
<220> FEATURE:
<223> OTHER INFORMATION: Fusogenic peptide

<400> SEQUENCE: 12

Gly Leu Leu Gly Ala Ile Ala Gly Phe Ile Glu
1               5                   10

<210> SEQ ID NO 13
<211> LENGTH: 11
<212> TYPE: PRT
<213> ORGANISM: Unknown
<220> FEATURE:
<223> OTHER INFORMATION: Fusogenic peptide

<400> SEQUENCE: 13

Gly Leu Phe Ala Ala Ile Ala Gly Phe Ile Glu
1               5                   10

<210> SEQ ID NO 14
<211> LENGTH: 11
<212> TYPE: PRT
<213> ORGANISM: Unknown
<220> FEATURE:
<223> OTHER INFORMATION: Fusogenic peptide

<400> SEQUENCE: 14

Gly Leu Phe Glu Ala Ile Ala Gly Phe Ile Glu
1               5                   10

<210> SEQ ID NO 15
<211> LENGTH: 11
```

```
<212> TYPE: PRT
<213> ORGANISM: Unknown
<220> FEATURE:
<223> OTHER INFORMATION: Fusogenic peptide

<400> SEQUENCE: 15

Gly Leu Phe Gly Ala Met Ala Gly Phe Ile Glu
1               5                   10

<210> SEQ ID NO 16
<211> LENGTH: 11
<212> TYPE: PRT
<213> ORGANISM: Unknown
<220> FEATURE:
<223> OTHER INFORMATION: Fusogenic peptide

<400> SEQUENCE: 16

Gly Leu Phe Gly Ala Ile Ala Gly Leu Ile Glu
1               5                   10

<210> SEQ ID NO 17
<211> LENGTH: 11
<212> TYPE: PRT
<213> ORGANISM: Unknown
<220> FEATURE:
<223> OTHER INFORMATION: Fusogenic peptide

<400> SEQUENCE: 17

Gly Leu Phe Gly Ala Ile Ala Gly Phe Ile Val
1               5                   10

<210> SEQ ID NO 18
<211> LENGTH: 20
<212> TYPE: PRT
<213> ORGANISM: Unknown
<220> FEATURE:
<223> OTHER INFORMATION: Fusogenic peptide

<400> SEQUENCE: 18

Gly Leu Phe Glu Ala Ile Ala Glu Phe Ile Glu Gly Gly Trp Glu Gly
1               5                   10                  15

Leu Ile Glu Gly
            20

<210> SEQ ID NO 19
<211> LENGTH: 20
<212> TYPE: PRT
<213> ORGANISM: Unknown
<220> FEATURE:
<223> OTHER INFORMATION: Fusogenic peptide

<400> SEQUENCE: 19

Gly Leu Leu Glu Ala Leu Ala Glu Leu Leu Glu Gly Gly Trp Glu Gly
1               5                   10                  15

Leu Leu Glu Gly
            20

<210> SEQ ID NO 20
<211> LENGTH: 7
<212> TYPE: PRT
<213> ORGANISM: Simian virus 40

<400> SEQUENCE: 20

Pro Lys Lys Lys Arg Lys Val
1               5
```

```
<210> SEQ ID NO 21
<211> LENGTH: 17
<212> TYPE: PRT
<213> ORGANISM: Saccharomyces cerevisiae

<400> SEQUENCE: 21

Cys Gly Gly Ala Gly Thr Ala Cys Thr Gly Thr Cys Cys Thr Cys Cys
1               5                   10                  15

Gly

<210> SEQ ID NO 22
<211> LENGTH: 37
<212> TYPE: PRT
<213> ORGANISM: Unknown
<220> FEATURE:
<223> OTHER INFORMATION: c-jun protein

<400> SEQUENCE: 22

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val
        35

<210> SEQ ID NO 23
<211> LENGTH: 37
<212> TYPE: PRT
<213> ORGANISM: Unknown
<220> FEATURE:
<223> OTHER INFORMATION: c-fos protein

<400> SEQUENCE: 23

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu
        35
```

COMPLEX-FORMING PROTEINS

BACKGROUND OF THE INVENTION

Complex forming proteins are widespread in nature.

Fundamentally, these proteins can be assigned to the following groups:

antibodies which, with their antigen-binding sites, can bind specifically to the corresponding epitope of an antigen (which can also be another antibody)

protein complexes, such as occur, for example, in the activation of the clofting system or of the complement system ligand receptor interactions of very different types, for example
of antigens or their epitopes with the Tcell or B-cell receptor
of growth factors, cytokines, chemokines, peptide hormones, steroid hormones and mediators with their respective receptors
of enzymes such as, for example, uPA or tPA with its receptor
of virus proteins with their respective cell receptor
adhesions between adhesion molecules protein complexes in signal transmission, control of the cell cycle and control of the transcription of genes Numerous examples of this are summarized in the literature, i.e. by Hardie et al., The Protein Kinase Facts Book I and II, Academic Press 1995, Callard et al., The Cytokine Facts Book, Academic Press 1994, Pigott et al., The Adhesion Molecule Facts Book, Academic Press 1994, Barclay et al., The Leukocyte Antigen Facts Book, Academic Press 1994, Watson et al., G-Protein Linked Receptor Facts Book, Academic Press 1994, Hesketh, The Oncogene Facts Book, Academic Press 1995, Leid et al., Cell 68, 377 (1992), Murre et al., Cell 58, 537 (1989), Bbeneza et al., Cell 61, 49 (1990), Brugge, Curr. Top. Microbiol. Immunolbiol. 123, 1 (1981), Callebaut et al., Proc. Natl. Acad. Sci. USA 89, 6270 (1992), Nadeau et al., J. Biol. Chem. 268, 1479 (1993), Burbach et al., Proc. Natl. Acad. Sci. USA 89, 8185 (1992), Hoffman et al., Science 252, 954 (1991), Stress-induced Proteins, M. L. Pardue, J. R. Feramisco and S. Lindquist Ed, A. R. Liss, New York (1989), Eukaryotic Transcription Factor, D. S. Lachman, Academic Press (1991), Transcriptional Regulations, Eds. S. McKnight and K. R. Yamamoto, CSHL Press, Cold Spring Harbor, New York (1992).

In some cases, the largely specific naturally occurring complexes formed, between at least two proteins, are utilized for the analysis or detection of proteins in the diagnosis of diseases (for this see EP 0 491 362 B1) and the binding partners of such proteins are used for the prophylaxis or therapy of disorders. If one partner of the particular protein complexes is available, with the aid of this partner the amount of the second or further component, be it, for example, complement or clotting factors, antigens, receptors or signal proteins, can be determined. Moreover, specific protein complexes are utilized in the search for small-molecule activators or inhibitors. In addition, purified antibodies or ligands for receptors, such as, for example, cytokines and peptide hormones, are administered to patients or animals for the prophylaxis or therapy of disorders.

In the case of these different application possibilities for proteins which form protein complexes, the specificity with which the respective proteins enter into complex formation and in addition the distribution of the respective proteins in the organism is of crucial importance. The lower the specificity, the more frequently nonspecific binding of a partner to foreign proteins will occur.

For example, nonspecific, i.e. undesired, formation of complexes with foreign protein partners is, as is known, the main problem of analysis and diagnosis using antibodies. Undesired formation of complexes with foreign protein partners can also be the cause of side effects in vivo, for example after injection of antibodies. In addition, the specific exclusive binding between two proteins is an essential prerequisite for the production and specific function of complex transcription factors, in particular of synthetic transcription factor complexes, such as have been described in the Patent Application EP-A 0 805 209.

There is thus a considerable need for novel, highly specific complex-forming proteins which do not react with foreign partners.

SUMMARY OF THE INVENTION

The invention relates to a complex formed from specifically complex-forming proteins which are not naturally occuring, wherein the following components are contained in the complex:

a) at least one ligand specific for a target structure, b) at least one protein comprising a mutated dimerization domain, the mutated dimerization domain having been derived, i.e, obtained, by mutation of a naturally occurring dimerization domain, it being possible for this mutated dimerization domain to interact specifically, i.e., bind specifically, with component c) and the component b) being bonded covalently to the component a), c) at least one protein comprising a mutated dimerization domain, the mutated dimerization domain having been derived, i.e., obtained, by mutation of a naturally occurring dimerization domain, it being possible for this mutated dimerization domain to interact specifically, i.e., bind specifically, with component b) and the component c) being bonded covalently to the component d), and d) at least one effector.

According to the invention, a characteristic of the components b) and c) is that in naturally occurring peptides or proteins of identical or different type amino acids are replaced or inserted such that the peptides or proteins mutated in this way can complex virtually only exclusively with one another. A complexation of peptides or proteins mutated in this way with the corresponding nonmutated wild-type proteins or peptides does not occur, however. In this way, homodimers or heterodimers of mutated monomers (mutated peptides or proteins) can be formed.

The mutations in the binding domains of the identical or different proteins therefor have the purpose of preventing the ability for complex formation between an unmutated monomer and a mutated monomer of a pair of identical or different proteins or peptides which would complex in the unmutated state. At the same time, the mutations impart to such a pair of mutated proteins the ability to bind to one another with high specificity. The mutations thus occur in pairs, where one mutation is present in component b), the other in component c), i.e. such that a molecular interaction is possible between the respective amino acids of such a pair.

Amino acids according to the invention inserted into naturally occurring peptides or proteins can be, for example (the listing in pairs is intended to indicate the molecular interaction in the context of a dimeric protein complex):

| Component b) or c) | Component c) or b) |
|---|---|
| 3-18 cysteines | 3-18 cysteines |
| 3-24 basic amino acids such as histidine, arginine, lysine | 3-24 acidic amino acids such as asparagine, asparic acid, glutamine, glutamic acid |
| 3-24 hydrophobic amino acids such as methionine, isoleucine, leucine, valine | 3-24 aromatic amino acids phenylalanine, tyrosine, tryptophan |
| 3-24 aromatic amino acids | 3-24 aromatic amino acids |

The starting proteins for components b) and c) can be identical or different here.

In a preferred embodiment, the binding constant of a complex of two proteins according to the invention is at least $K_M=10^{-7}$ mol $l^{-1}$, preferably at least $K_M=10^{-8}$ mol $l^{-1}$.

Within the meaning of this invention, the following identical or unidentical partners (for the production of component b) or c) and with the aim of binding heterodimers), for example, are preferably mutated in their respective binding domain and these or the entire protein are used:

| Component b) or c) | Component c) or b) |
|---|---|
| Fos | Jun or Jun B or Jun D |
| FRAU-1 | Jun or Jun B or Jun D |
| FRAU-2 | Jun or Jun B or Jun D |
| FOS-B | Jun or Jun B or Jun D |
| OCT-1 | Jun or Jun B or Jun D |
| NFKB (p65) | IKB |
| Ras | RAF |
| CD4 | p56LcK |
| bcl-2 | bad or bax |
| cyclin A | cdk1 |
| E2F | DP |
| CD40 | CD40L |
| Myc | Max |
| Myc N | Max |
| Myc L | Max |
| p105 (Rb1) | AFF-2, E1A |
| p107 (Rb2) | E7, E2F or Myc |
| p130 | E7, E2F or Myc |
| CBL | Gag |
| TRP | TRP |
| Met | Met |
| Myb | p67 or p160 |
| VAV | p67 or p160 |
| APC | α- or β-Catenin |
| APC | APC |
| VD receptor | h-(Retinoid x-receptor)RXR α or β |
| T3 receptor | HRXR α or β |
| MyoD | E12 |
| Component b) or c) | Component c) or b) |
| E12 | Id |
| E47 | Id |
| hHSP90 | Progesterone receptor |
| hHSP90 | Glucocorticoid receptor |
| hHSP90 | Mineral corticoid receptor |
| hHSP90 | Dioxin receptor |
| Dioxin receptor | Arnt |
| HPS90 | FKBP59 |
| HSP90 | Cyclosporin-binding protein |
| HPS90 | pp60$^{V-src}$ |
| HSP70 | HSF1 Heat shock factor 1 |
| HSP70 | HSF2 Heat shock factor 2 |

Those protein pairs are to be preferred which naturally have a helix-loop-helix/leucine zipper binding sequence.

The invention additionally relates to the very different uses of these complex-forming proteins according to the invention, for example as multivalent protein complexes for prophylaxis and therapy as multivalent ligands for vectors for gene therapy as synthetic transcription factors for control of the expression of genes and as diagnostic or analytical systems.

It is understood that these applications can either be accomplished in vivo or in vivo. Furthermore, it is understood that the gene therapy applications can be for either in vivo or ex vivo gene therapy, as these techniques are understood in the art.

In this context, the components a) and d) are selected depending on the chosen type of use.

The invention relates particularly to novel complex-forming proteins, wherein the amino acids mentioned have been inserted into proteins which naturally form homodimers or heterodimers, such that these proteins (components b) and c)) mutated in this way only form complexes with themselves (homodimers) or with the correspondingly mutated partner (heterodimers), but no longer with the naturally occurring, nonmutated starting proteins.

Novel complex-forming proteins containing the components a), b), c) and d) can be used in, for example, two embodiments.

In the first embodiment (see FIG. 1a), the component b) is a homo- (or hetero)multimer [component b)1–b)n], to which the corresponding identical (or different) components c) in each case bind, in each case as a monomer and in each case linked to the component d).

With this embodiment, many components d) (effectors) are bound to the target structure.

In the second embodiment (see FIG. 2), both the component b) and the component c) are multimers, only one or a few components d) being bound to the component c). Although with this embodiment only a few components d) (effectors) are bound to the target structure, the binding between the components c) and d) is extremely strong, which can increase the specificity of the binding of the components c) and d) to the target structure.

The invention relates to novel, complex-forming proteins consisting of the components a), b), c) and d), and also nucleic acid constructs which code for these complex-forming proteins. The invention likewise relates to complexes consisting of the components d), b), c) and d), i.e. the component a) is replaced by d), and nucleic acid constructs coding therefor.

In addition, the invention relates to a complex consisting of the components a), b), c) and a); i.e. the component d) is replaced by a), and nucleic acid constructs coding therefor.

The invention furthermore also relates to complex-forming proteins consisting of the components a), b), c) and d) or variants thereof described above, which additionally contain a fusogenic peptide, a translocation peptide or, between the components c) and d) or a) and b), a cleavage sequence for a protease, and nucleic acid constructs coding therefor.

All such nucleic acid constructs of this type can be introduced into bacteria, yeasts or mammalian cells with the aid of viral or nonviral vectors known to the person skilled in the art.

Cells of this type can be used for the preparation of the protein according to the invention or even administered for the purpose of the prophylaxis or therapy of an organism.

Nucleic acid constructs of this type, inserted in a vector, however, can also be administered directly to an organism for the purpose of prophylaxis or therapy.

The invention furthermore relates to the preparation of one of the abovementioned complexes, in which a protein of this complex is expressed with the aid of a nucleic acid construct coding therefor and a further protein of this complex, which is different from the first, is expressed with the aid of a nucleic acid construct coding therefor, and the expressed proteins are isolated and complexed with one another. In the case of complexes consisting of homodimers or homooligomers, the preparation is carried out without the expression of a second protein which is different from the first.

The invention further relates to:

A complex comprising the following components:
- a) at least one ligand specific for a target structure;
- b) at least one protein comprising a mutated dimerization domain obtained by mutation of a naturally occurring dimerization domain, wherein the mutated dimerization domain binds specifically with component c) and the component b) is covalently bonded to the component a);
- c) at least one protein comprising a mutated dimerization domain obtained by mutation of a naturally occurring dimerization domain, wherein the mutated dimerization domain binds specifically with the component b) and the component c) is covalently bonded to component d); and
- d) at least one effector;
  wherein the components b) and c) are not naturally occurring proteins.

The above complex, wherein the component a) is replaced by the component d).

The above complex, wherein the component d) is replaced by the component a).

The above complex, which further comprises a fusogenic peptide or a translocalization peptide.

The above complex, which further comprises a cleavage sequence for a protease between the components c) and d) or a) and b).

The above complex, wherein the component a) is selected from the group consisting of: a growth factor, a cytokine, TNF, a chemokine, a peptide hormone, a mediator, a steroid hormone, a vitamin, a complement factor, a clotting factor, a kinin system factor, a fibrinolysis system factor, a plasmatic enzyme, a cell enzyme, a plasmatic enzyme inhibitor, a cell enzyme inhibitor, a virus coat protein, a cell receptor for the afore-mentioned molecules, an antibody, an antibody cleavage product, a DNA binding protein, a DNA binding domain of a transcription factor and an activation domain of a transcription factor.

The above complex, wherein the components b) and c) are obtained by mutating the naturally occurring dimerization domains of proteins which bind naturally to one another.

The above complex, wherein the naturally occurring dimerization domains of components b) and c) are selected from the group of naturally dimerizing partners consisting of:

| | |
|---|---|
| Fos | Jun or Jun B or Jun D; |
| FRAU-1 | Jun or Jun B or Jun D; |
| FRAU-2 | Jun or Jun B or Jun D; |
| FOS-B | Jun or Jun B or Jun D; |
| OCT-1 | Jun or Jun B or Jun D; |
| NFKB (p65) | IKB; |
| Ras | RAF; |
| CD4 | p56Lck; |

-continued

| | |
|---|---|
| bcl-2 | bad or bax; |
| Cyclin A | cdk1; |
| E2F | DP; |
| CD40 | CD40L; |
| Myc | Max; |
| Myc N | Max; |
| Myc L | Max; |
| p105 (Rb1) | AFF-2, E1A; |
| p107 (Rb2) | E7, E2F or Myc; |
| p130 | E7, E2F or Myc; |
| CBL | Gag; |
| TRP | TRP; |
| Met | Met; |
| Myb | p67 or p160; |
| VAV | p67 or p160; |
| APC | α- or β-Catenin; |
| APC | APC; |
| VD receptor | h-(Retinoid x-receptor)RXR α or β; |
| T3 receptor | HRXR α or β; |
| MyoD | E12; |
| E12 | Id; |
| E47 | Id; |
| HHSP90 | Progesterone receptor; |
| HHSP90 | Glucocorticoid receptor; |
| HHSP90 | Mineralocorticoid receptor; |
| HHSP90 | Dioxin receptor; |
| Dioxin receptor | Arnt; |
| HPS90 | FKBP59; |
| HSP90 | Cyclosporin-binding protein; |
| HPS90 | $Pp60^{V-src}$; |
| HSP70 | HSF1 heat shock factor 1; and |
| HSP70 | HSF2 heatshock factor 2. |

The above complex, wherein the naturally dimerizing partners belong to the helix-loop-helix/leucine zipper family of proteins.

The above complex, wherein the mutated dimerization domains are obtained by inserting:
- 3–18 cysteines in the naturally occurring dimerization domain in at least one of the proteins of component b) and in at least one of the proteins of component c);
- 3–24 basic amino acids in the naturally occurring dimerization domain in at least one of the proteins of component b) and 3–24 acidic amino acids in the naturally occurring dimerization domain in at least one of the proteins of component c);
- 3–24 basic amino acids in the naturally occurring dimerization domain in at least one of the proteins of component c) and 3–24 acidic amino acids in the naturally occurring dimerization domain in at least one of the proteins of component b);
- 3–24 hydrophobic amino acids in the naturally occurring dimerization domain in at least one of the proteins of component b) and 3–24 aromatic amino acids in the naturally occurring dimerization domain in at least one of the proteins of component c);
- 3–24 hydrophobic amino acids in the naturally occurring dimerization domain in at least one of the proteins of component c) and 3–24 aromatic amino acids in the naturally occurring dimerization domain in at least one of the proteins of component b); and/or
- 3–24 aromatic amino acids in the naturally occurring dimerization domain in at least one of the proteins of component b) and 3–24 aromatic amino acids in the naturally occurring dimerization domain in at least one of the proteins of component c).

The above complex, in which the components b) and c) are mutated binding domains of c-fos and c-jun, comprising the following mutations:

c-fos amino acid 167E→K
172E→K
181E→K c-jun amino acid 283K→E
288K→E
302K→E

The above complex, wherein the component d) is selected from the group consisting of: inhibitors of cell proliferation, apoptosis-inducing proteins, cytostatic proteins, cytotoxic proteins, coagulation-inducing factors, angiogenesis-inducing factors, angiogenesis-inhibiting factors, growth factors, cytokines, chemokines, interleukins, interferons, complement factors, clotting factors, fibrinolysis-inducing proteins, peptide hormones, mediators, bacterial proteins, receptors, viral antigens, parasitic antigens, tumor antigens, autoantigens, tissue antigens, adhesion molecules, antibodies, antibody cleavage products, enzymes for reacting with a signal-emitting component, enzymes for converting a precursor of an active substance into an active substance, fluorescent dyes, isotopes, metal-binding proteins, and a DNA-binding domain.

A method for treating diseased cells, wherein the disease results from inflammation, autoimmune diseases, defective formation of blood cells, nervous system damage, blood-clotting system disorders, blood circulation system disorders, tumor formation, viral infections, or bacterial infections, comprising administering the above complex to the cells.

A method for introducing a vector into a cell of an organism or cell culture, comprising binding the above complex to a viral or nonviral vector and introducing the vector into the cell of an organism or a cell culture in a cell-specific manner.

A method of detecting the presence or amount of a reactant in vitro or in vivo, comprising contacting the above complex with the reactant, either in vivo or in vitro, wherein the component a) binds to the reactant and the component d) emits a signal, such that the presence or amount of the reactant is detected by measuring the amount of the emitted signal.

A nucleic acid construct coding for a protein of the above complex.

The nucleic acid construct as above, coding for an activator subunit of an activator-responsive promoter unit.

A host cell comprising the nucleic acid construct as above.

The host cell as above, selected from the group consisting of a bacterium, a yeast and a mammalian cell.

A method of expressing a protein of the above complex, comprising expressing a nucleic acid encoding the protein in a host cell under conditions such that the protein is expressed in a detectable amount.

A method of producing a complex between the component b) and the component c) as in the above complex, comprising:

(a) expressing the at least one protein of the component b) by translating a nucleic acid construct encoding the protein;

(b) expressing the at least one protein of the component c) by translating a nucleic acid construct encoding the protein;

(c) isolating the proteins of steps (a) and (b);

(d) contacting the at least one protein of step a) with the at least one protein of step b) under conditions such that the proteins bind to one another.

The above complex, wherein the antibody cleavage product is selected from the group consisting of: $F(ab)_2$, a single-chain Fv, a single-chain, a double antigen-binding molecule, and an Fc fragment.

The above complex, wherein the receptor is selected from the group consisting of receptors for: growth factors, cytokines, chemokines, interleukins, interferons, complement factors, clotting factors, fibrinolysis-inducing proteins, peptide hormones, steroid hormones, mediators, and virus coat proteins.

The above complex, wherein the antibody cleavage product is selected from the group consisting of: $F(ab)_2$, Fab, single-chain Fv, and single-chain double antigen-binding proteins.

A vaccine comprising the above complex.

A complex comprising the following components:

a) at least one ligand specific for a target structure;

b) at least one protein comprising a mutated dimerization, wherein the mutated dimerization domain binds specifically with component c) and the component b) is covalently bonded to the component a);

c) at least one protein comprising a mutated dimerization domain, wherein the mutated dimerization domain binds specifically with the component b) and the component c) is covalently bonded to component d); and d) at least one effector;

wherein the components b) and c) are not naturally occurring proteins.

The above complex, wherein at least one protein of component b) binds specifically with at least one protein of component c) with a binding constant of at least a $K_M$ of $10^{-7}$ mol $l^{-1}$.

(*b*) Variant of possibility 1

Figure 2:
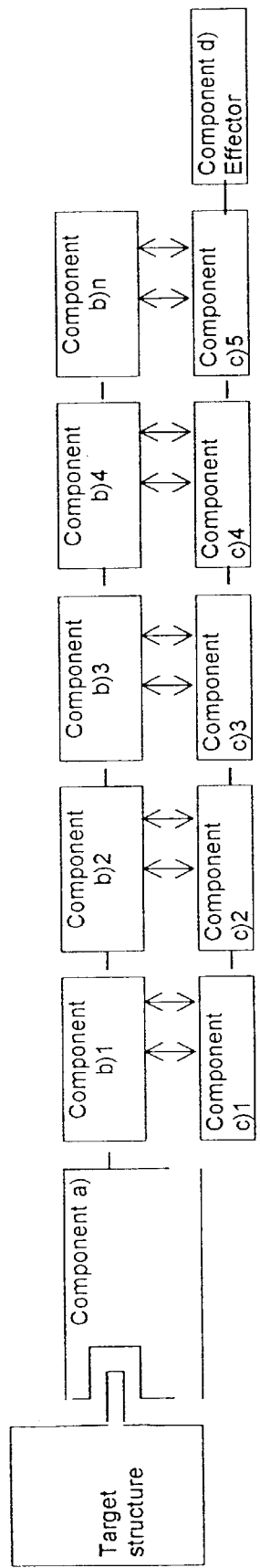

FIG. 2: Schematic representation of the novel complex-forming proteins possibility 2.

FIG. 3: Activator responsive promoter units A and B according to the examples.

FIG. 4: Mutations of c-jun and c-fos according to the examples.

Figure 5:
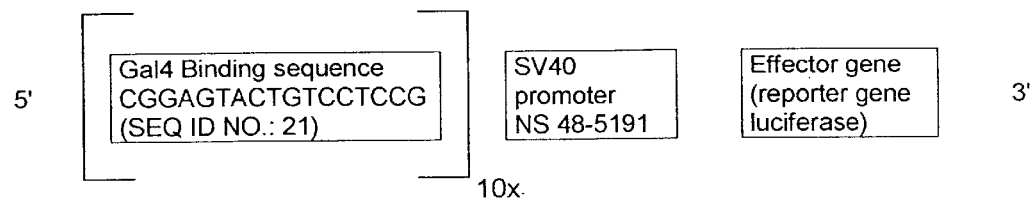

FIG. 5: The activator-responsive promoter and the effector gene.

Figure 6:
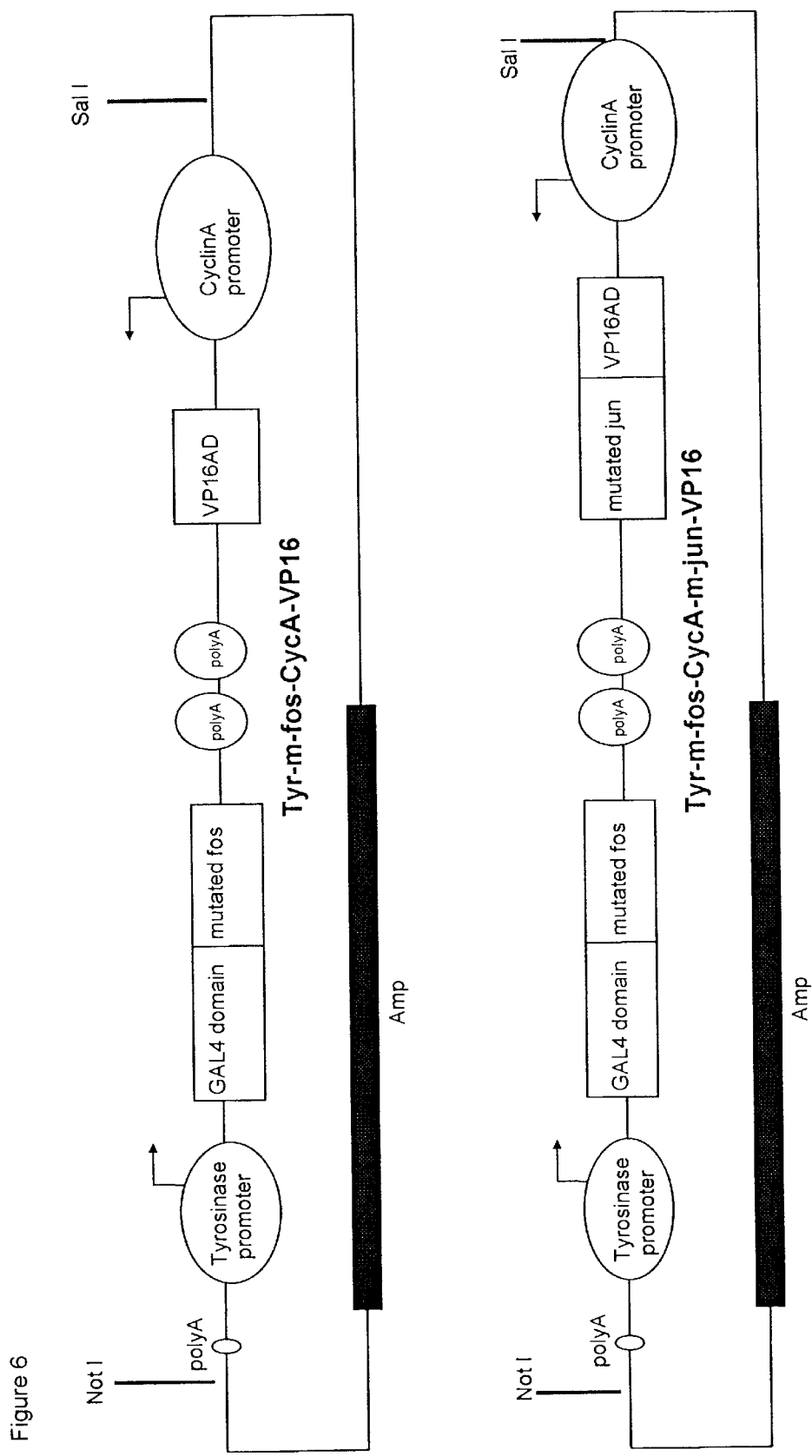

FIG. 6: Nucleic acid constructs for the expression of the complex-forming proteins according to the invention.

DETAILED DESCRIPTION OF THE PREFERRED EMBODIMENTS

As used herein, the term "binds specifically" when referring to the binding of a protein of component b) to a protein of component c) refers, preferably, to a binding constant of at least $K_M=10^{-7}$ mol $l^{-1}$, or at least approximately $K_M=10^{-8}$ mol $l^{-1}$, and more preferably at least $K_M=10^{-8}$ mol $l^{-1}$, or at least approximately $K_M=10^{-8}$ mol $l^{-1}$. In a further preferred embodiment, "binds specifically" connotes that the mutated binding domain will not bind, or will have essentially no binding, to the naturally occuring binding domain to which it binds in nature.

As used herein, the term "inserted" when referring to the insertion of mutations into naturally occurring dimerization domains connotes in a preferred embodiment that a substitution mutation is made by substituting or exchanging or replacing a naturally occuring amino acid with a different encodable amino acid. The insertion of the mutations described herein also includes addition mutations, meaning that the described insertion adds one or more additional amino acids to the naturally occuring binding domain.

Multivalent Protein Complexes for Prophylaxis and Therapy

The present invention relates to the use of the protein complexes according to the invention for the prophylaxis or therapy of a disorder. In this context, the component a) is a ligand for the target structure. This target structure can be present on a cell membrane, in the extracellular matrix or in a tissue or blood fluid.

According to the invention, the component a) can be
a ligand for a cell receptor, for example
growth factors such as VEGF, PDGF, EGF, TGFα, TGFβ, KGF, SDGF, FGF, IGF, HGF, NGF, BDNF, neurotrophins, BMF, bombesin, M-CSF, thrombopoietin, erythropoietin, SCF, SDGF, oncostatin, PDEGF, endothelin-1
cytokines such as IL-1, IL-2, IL-3, IL-4, IL-5, IL-6, IL-7, IL-8, IL-9, IL-10, IL-11, IL-12, IL-13, IL-14, IL-15
interferon α, β and γ
tumor necrosis factors TNFα, -β
chemokines such as RANTES, MCAF, MIP-1α or -β, NAP, β-thromboglobulin
peptide hormones such as SRH, SIH or STH, MRH or MSH, PRH, PIH or prolactin, GnRH, LH-RH, FSH-RH, LH/ICSH or FSH, TRH or TSH, CRH or ACTH
angiotensin, kinins, histamine, homologs or analogs thereof
steroid hormones such as estrogens, gestagens, androgens, glucocorticoids, mineralocorticoids, homologs or analogs thereof
vitamins such as, for example, folic acid In the context of the present invention, the component a) can also be an adhesion molecule, a part of the adhesion molecule or an analog of an adhesion molecule which binds to a corresponding adhesion molecule on the cell membrane or to another specific binding structure for an adhesion molecule on the target cell.

Adhesion molecules of this type capable of functioning as component a) are, for example
Lewis X (for GMP-140)
S-Lewis X (for ELAM-1).
LFA-1 (for ICAM-1 and ICAM-2)
MAC-1 (for ICAM-1)
VLA-4 (for VCAM-1)
PECAM (for PECAM)
Vitronectin (for the vitronectin receptor)
GMP-140 (for Lewis X)
S-Lewis X (for ELAM-1)
ICAM-1, ICAM-2 (for LFA-1, MAC-1)
VCAM-1 (for VLA-4)
Fibronectin (for VLA-4)
Laminin (for VLA-6)
Fibronectin, laminin (for VLA-1, VLA-2, VLA-3)
Fibronectin (for VLA-4)
Fibrinogen (for GPIIb-IIIa)
B7 (for CD28)
CD28 (for B7)
CD40 (for CD40L)
CD40L (for CD40)

In the context of the present invention, the component a) can also be a protein which is bound to a partner protein and thereby participates in a biological reaction chain, for example a complement factor, a clotting factor, a factor of the kinin system, of the fibrinolysis system or a plasmatic or cell enzyme inhibitor or a plasmatic or cell enzyme.

In the context of the present invention, the component a) can also be a receptor for one of the proteins mentioned beforehand.

In the context of the present invention, the component a) can also be the extracellular portion of an Fc receptor (Dougherty et al., Transfusion Science 17, 121 (1996)), to which an antibody specific for the target cell is bounded via its Fc portion.

In the context of the present invention, the component a) can also be an antibody molecule or the epitope-binding part of an antibody molecule. Human antibodies are to be preferred.

The murine monoclonal antibodies can be employed in humanized form. Humanization is carried out in the manner shown by Winter et al. (Nature 349, 293 (1991)) and Hoogenbooms et al. (Rev. Tr. Transfus. Hemobiol. 36, 19 (1993)). Antibody fragments are prepared according to the prior art, for example in the manner described by Winter et al., (Nature 349, 293 (1991)), Hoogenboom et al. (Rev. Tr. Transfus. Hemobiol. 36,19 (1993), Girol, Mol. Immunol. 28, 1379 (1991)) or Huston et al. (Int. Rev. Immunol. 10, 195 (1993)).

Recombinant antibody fragments are prepared directly from existing hybridomas or are isolated from libraries of murine or human antibody fragments with the aid of "phage display" technology. These antibody fragments are then employed at the genetic level directly for further manipulations (e.g. fusion with other proteins).

For the production of recombinant antibody fragments from hybridomas, the genetic information which codes for the antigen-binding domains (VH, VL) of the antibodies is obtained by isolation of the mRNA, reverse transcription of the RNA into cDNA and subsequent amplification by means of polymerase chain reaction and oligonucleotides complementary to the 5' or 3' ends of the variable fragments. The VH and VL fragments are then cloned into bacterial expression vectors, e.g. in the form of Fv fragments, single-chain Fv fragments (scFv) or as Fab fragments.

Novel antibody fragments can also be isolated directly from antibody libraries (immunolibraries, native libraries) of murine or human origin by means of the "phage-display" technology. In the "phage display" of antibody fragments, the antigen-binding domains are cloned as fusion proteins with the coat protein g3P of filamentous bacteriophages either into the phage genome or into phagemid vectors in the form of scFv fragments or as Fab fragments. Antigen-binding phages are selected on antigen-coated plastic containers ("panning"), on antigen-conjugated, paramagnetic beads or by binding to cell surfaces.

Immunolibraries are prepared by PCR amplification of the variable antibody fragments from B lymphocytes of immunized animals or patients. For this, combinations of oligonucleotides which are specific for murine or human immunoglobulin genes or for the human immunoglobulin gene families are used.

Using nonimmunized donors as the source of the immunoglobulin genes, native libraries can be prepared. Alternatively, immunglobulin germ line genes can be employed for the preparation of semisynthetic antibody repertoires, the complementarity-determining region 3 of the variable fragments being replaced by PCR with the aid of degenerated primers. These so-called single pot libraries have the advantage, compared with immunolibraries, that antibody fragments against a large number of antigens can be isolated from a single library.

The affinity of antibody fragments can be further increased by means of the phage display technology, new libraries of already existing antibody fragments being prepared by random, codon-based or targeted mutagenesis, by chain shuffling of individual domains with fragments from native repertoires or with the aid of bacterial mutator strains and antibody fragments having improved properties being isolated by reselection under stringent conditions. In addition, murine antibody fragments can be humanized by stepwise replacement of one of the variable domains by a human repertoire and subsequent selection using the original antigen (guided selection). Alternatively, the humanization of murine antibodies is carried out by target-directed replacement of the hypervariable regions of human antibodies by the corresponding regions of the original murine antibody.

According to the invention, at least two identical or different ligands for the target structure, e.g. on the target cell, can be contained in the ligand according to the invention (component a). A particular form of bispecific or multispecific, recombinant antibodies are single-chain, double- or multiple-antigen-binding molecules. The preparation of these molecules was described in the Patent Application DE 19816141.7 (not published). In this patent application, reference is made expressly, for example, to the preparation of the component a).

In the context of the present invention, the component a) can also be the coat protein or a part of the coat protein of viruses which specifically bind to selected cells by means of their coat protein.

The choice of the component a) depends on the target structure to which the complex-forming protein according to the invention is to bind.

Examples of these are:

Ligands for Activated Endothelial Cells

Within the meaning of the invention, these include antibodies or antibody fragments, directed against membrane structures of endothelial cells, such as have been described, for example, by Burrows et al. (Pharmac. Ther. 64, 155 (1994), Hughes et al. (Cancer Res. 49, 6214 (1989)) and Maruyama et al. (PNAS-USA 87, 5744 (1990)). In particular, these include antibodies against the VEGF receptors.

The ligands additionally include all active compounds which bind to membrane structures or membrane receptors on endothelial cells. These include, for example, substances which, terminally, contain mannose, in addition IL-1 or growth factors or fragments thereof or subsequences of them, which bind to receptors expressed by endothelial cells, such as, for example, PDGF, bFGF, VEGF, TGFβ (Pusztain et al., J. Pathol. 169, 191 (1993)).

In addition, these include adhesion molecules which bind to activated and/or proliferating endothelial cells. Adhesion molecules of this type, such as, for example, Slex, LFA-1, MAC-1, LECAM-1, VLA-4, vitronectin or RGD peptides have already been described (reviews in Augustin-Voss et al., J. Cell Biol. 119, 483 (1992), Pauli et al., Cancer Metast. Rev. 9, 175 (1990), Honn et al., Cancer Metast. Rev. 11, 353 (1992)).

The ligands within the meaning of this invention in particular include coat glycoproteins of viruses which have a tropism for endothelial cells. These viruses include, for example:

Filoviruses, for example
- the Marburg virus with its coat protein GP (glycoprotein) and sGP (second glycoprotein)
- or the Ebola virus in each case with its coat protein GP and sG the cytomegalovirus particularly with its gB protein the herpes simplex virus type I the HIV-1 virus the measles virus the Hantaan virus alphaviruses, such as Semliki forest virus the epidemic, hemorrhagic fever virus the polio virus enteroviruses (such as, for example, Echo 9, Echo 12, Coxsackie B3)

Ligands for Activated Macrophages and/or Activated Lymphocytes

The ligands within the meaning of the invention include further substances which specifically bind to the surface of immune cells. These include antibodies or antibody fragments directed against membrane structures of immune cells, such as have been described, for example, by Powelson et al. (Biotech. Adv. 11, 725 (1993)).

In addition, the ligands also include monoclonal or polyclonal antibodies or antibody fragments which bind with their antigen-binding variable portion to Fc-γ or Fc-ε or Fc-μ receptors of immune cells (Rojanasakul et al., Pharm. Res. 11, 1731 (1994)).

In addition, this includes the Fc fragment of human monoclonal or polyclonal immunoglobulin. Fc fragments of this type are prepared, for example, by genetic engineering with the aid of recombinant DNA or according to the methods of Haupt et al. (Klin. Wschr. 47, 270 (1969)), Kranz et al. (Dev. Biol. Standard 44, 19 (1979)), Fehr et al. (Adv. Clin. Pharmac. 6, 64 (1974)) or Menninger et al. (Immunochem. 13, 633 (1976)).

The ligands additionally include all substances which bind to membrane receptors on the surface of immune cells. These include cytokines such as, for example, IL-1, IL-2, IL-3, IL-4, IL-6, IL-10, TNFα, GM-CSF, M-CSF, in addition growth factors such as, for example, EGF, TGF, FGF, IGF or PDGF or fragments thereof or subsequences of them which bind to receptors expressed by immune cells. These additionally include adhesion molecules and other ligands which bind to cell membrane structures, such as, for example, to the mannose 6-phosphate receptor on macrophages in the spleen, liver, lung and other tissues.

A selection of these ligands and membrane structures are clearly described in Perales et al. (Eur. J. Biochem. 226, 255 (1994)).

The ligands within the meaning of this invention, however, also include coat glycoproteins of those viruses which have a tropism for lymphocytes and/or macrophages.

These viruses infecting macrophages include, for example:

HIV-1 particularly those strains having mutations in the V3 region of gp120, which lead to an increased binding to macrophages

HIV-2

Hanta viruses, for example the Punmala virus cytomegalovirus respiratory syncytial virus herpes simplex virus filoviruses.

The viruses infecting lymphocytes include, for example:

varicella zoster virus (VZV);

VZV particularly infects T cells herpes virus 6 (HHV-6);
  HHV-6 particularly infects T cells
rabies virus;
  the rabies virus coat protein particularly binds to TH2 cells
HIV-1;
  the glycoprotein gp120 preferably binds to the CD4 molecule of T cells
HTLV-II;
  HTLV-II particularly infects B cells
HTLV-I;
  HTLV-I particularly infects T cells
influenza C viruses;
  influenza C viruses bind by means of the hemagglutinin esterase fusion (HEF) protein to N-acetyl-9-O-acetyineuraminic acid (Neu 5,9 Ac), which preferably occurs on B lymphocytes, to a lesser extent or not on T lymphocytes
influenza C viruses having a mutation in the nucleotide position 872 (which encodes the position 284 of the HEF of the amino acid sequence), for example a replacement of the threonine by isoleucine. The surface protein HEF having this mutation has a distinctly stronger affinity for the N-acetyl-9-O-acetylneuraminic acid receptor than the wild virus HEF cleavage products of the influenza C virus, which contain the binding structure for N-acetyl-9-O-acetyineuraminic acid. This binding structure is defined by the catalytic triad serine 71, histidine 368 or 369 and aspartic acid 261

Epstein-Barr virus;
- EBV particularly infects B cells herpes simplex virus-2;
- HSV-2 particularly infects T cells measles virus Ligands for Muscle Cells These include, for example, antibodies or antibody fragments directed against membrane structures of muscle cells, in particular of smooth muscle cells. Antibodies of this type are, for example

- the antibody 10F3
- antibodies against actin
- antibodies against angiotensin II receptors
- antibodies against receptors for growth factors or antibodies directed, for example, against
- EGF receptors
- or against PDGF receptors
- or against FGF receptors
- or antibodies against endothelin A receptors.

The ligands additionally include all active substances which bind to membrane structures or membrane receptors on muscle cells (review in Pusztai et al., J. Pathol. 169, 191 (1993), Harris, Curr. Opin. Biotechnol. 2, 260 (1991)). For example, these include growth factors or fragments thereof or subsequences of them which bind to receptors expressed by smooth muscle cells such as, for example

- PDGF
- EGF
- TGFβ
- TGFα
- FGF
- endothelin A

The ligands within the meaning of this invention, however, also include glycoproteins of the coat of those viruses which have a tropism for muscle cells. These viruses include, for example, the cytomegalovirus.

Ligands for Hematogenic Cells

The ligands include antibodies or antibody fragments directed against receptors expressed on poorly differentiated blood cells.

Antibodies of this type have been described, for example, for the following receptors:

- stem cell factor receptor
- IL-1 receptor (type I)
- IL-1 receptor (type II)
- IL-3 receptor α
- IL-3 receptor β
- IL-6 receptor
- GM-CSF receptor.

In addition, the ligands also include monoclonal or polyclonal antibodies or antibody fragments which, with their constant domains, bind to Fc-γ receptors of immune cells.

The ligands additionally include all substances which bind to membrane structures or membrane receptors on the surface of poorly differentiated blood cells. For example, these include growth factors, such as SCF, IL-1, IL-3, IL-6, GM-CSF or fragments thereof or subsequences of them which bind to receptors expressed by blood cells.

Ligands for Synovial Cells and Inflammatory Cells

These include monoclonal or polyclonal antibodies or antibody fragments which bind with their variable domains to membrane structures of synovial cells or inflammatory cells. Such membrane structures are, for example,

- vimentin
- fibronectin or
- Fc receptors.

These also include monoclonal or polyclonal antibodies or antibody fragments which bind with their constant domains to the Fc receptor.

These additionally include all active compounds which bind to membrane structures or membrane receptors on synovial cells. For example, included here are cytokines or growth factors or fragments thereof or subsequences of them which bind to synovial cells expressed on receptors, such as, for example, IL-1-RA, TNFα, IL4, IL-6, IL-10, IGF, TGFβ.

In addition, these include ligands whose essential constituent is terminal mannose which binds to mannose-6-phosphate receptors on macrophages.

Ligands for Cells Infected with Viruses

The ligands include antibodies or antibody fragments directed against the virus antigens expressed on the cell membrane of virus-infected cells.

Antibodies of this type have been described, for example, for cells infected with the following viruses:

- HBV
- HCV
- HSV
- HPV
- HIV
- EBV
- HTLV.

Ligands for Liver Cells and Further Tissue Cells

The ligands include all substances which bind to membrane structures or membrane receptors on the surface of liver cells. For example, these include growth factors, such as cytokines, EGF, TGF, FGF or PDGF, or fragments thereof or subsequences of them which bind to receptors expressed by cells of this type. These additionally include ligands which bind to cell membrane structures which are selective for certain tissues. These include, for example:

| Membrane structure | Ligand | Tissue cells |
|---|---|---|
| Asialoglycoprotein receptor | Asialoorosomucoid Neoglycoprotein Galactose | Liver cells |
| Transferrin receptor | Transferrin | Liver, other tissue cells |
| Insulin receptor | Insulin | Liver, other tissue cells |
| Mannose-6-phosphate receptor | Mannose | Macrophages in spleen, liver, lung, other tissues |
| Fc-γ receptors | Immunoglobulin G | Reticuloendothelial system, other tissues |

These ligands and membrane structures are described clearly in Perales et al. (Eur. J. Biochem. 226, 255 (1994)).

The ligands within the meaning of the invention, however, particularly include coat glycoproteins of viruses which have a tropism for selected cells, such as, for example, for Bronchial epithelial cells
  respiratory syncytial virus
Liver cells
  hepatitis C virus, hepaptitis B virus, hepatitis A virus
  Filoviruses
    Liver cells bind, for example, the Marburg virus by means of the asialoglycoprotein receptor
  Hepatitis B virus
    Liver cells preferably bind by means of the asialoglycoprotein receptor to the preS2 and preS1 domains of HBV
- Hepatitis D virus Liver sinusoidal cells
- Hepatitis V virus
  - HBV is bound by means of fibronectin.

Ligands for Glia Cells

These include antibodies or antibody fragments directed against membrane structures of glia cells, such as have been reported, for example, by Mirsky et al. (Cell and Tissue Res. 240, 723 (1985)), Coakham et al. (Prog. Exp. Tumor Res. 29, 57 (1985)) and McKeever et al. (Neurobiol. 6, 119 (1991)). These membrane structures furthermore include neural adhesion molecules such as N-CAM, in particular its C polypeptide chain.

These additionally include all active compounds which bind to membrane structures or membrane receptors on glia cells. For examples, these include substances which carry mannose terminally and bind to the mannose-6-phosphate receptor, insulin and insulin-like growth factor, PDGF and those fragments of these growth factors which bind to the associated membrane receptors.

The ligands within the meaning of the invention in particular include coat glycoproteins of those viruses which have a tropism for glia cells.

These viruses include, for example:

HIV-1 subtype JRF1 herpes simplex virus I

Ligands for Leukemia Cells

These include antibodies or antibody fragments directed against membrane structures of leukemia cells. A large number of monoclonal antibodies of this type have already been described for diagnostic and therapeutic procedures (reviews in Kristensen, Danish Medical Bulletin 41, 52 (1994); Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)). Depending on the type of leukemia, suitable ligands are, for example, monoclonal antibodies or antigen-binding antibody fragments thereof having specificity for the following antigens:

| Cells | Membrane antigen |
|---|---|
| AML | CD13<br>CD14<br>CD15<br>CD33<br>CAMAL<br>Sialosyl-Le |
| B-CLL | CD5<br>CD1c<br>CD23<br>Idiotypes and isotypes of the membrane immunoglobulins |
| T-CLL | CD33<br>M38<br>IL-2 receptors<br>T cell receptors |
| ALL | CALLA<br>CD19<br>Non-Hodgkin lymphoma |

The ligands additionally include all active compounds which bind to membrane structures or membrane receptors of leukemia cells. For example, these include growth factors or fragments thereof and subsequences of them which bind to receptors expressed by leukemia cells.

Growth factors of this type have already been described (reviews in Cross et al., Cell 64, 271 (1991); Aulitzky et al., Drugs 48, 667 (1994); Moore, Clin. Cancer Res. 1, 3 (1995); Van Kooten et al., Leuk. Lymph. 12, 27 (1993)). For example, they include:

IFNα in non-Hodgkin lymphomas

IL-2, particularly in T cell leukemias

FGF in T cell, monocytic, myeloid, erythroid and megakaryoblastic leukemias

TGFβ in leukemias retinoids, e.g. retinoic acid in acute promyelocytic leukemia.

Ligands for Tumor Cells

These include antibodies and fragments of these antibodies directed against membrane structures on tumor cells. Antibodies of this type have been clearly described, for example, by Sedlacek et al. (Contrib. to Oncol. 32, Karger Verlag, Munich (1988) and Contrib. to Oncol. 43, KargerVerlag, Munich (1992)).

Further examples are antibodies against:

sialyl Lewis peptides on tumors, which are recognized by T cells proteins expressed by oncogenes gangliosides such as GD3, GD2, GM2, 9-0-acetyl GD3, fucosyl GM1 blood group antigens and their precursors antigens on the polymorphic epithelial mucin antigens on heat shock proteins According to the invention, the component d) can either be absent or, depending on the nature of the disorder which is to be prevented or treated, is to be selected together with the component a), for example, as follows:

a) Therapy of Tumors a. 1) Target Cells:

proliferating endothelial cells or stroma cells and muscle cells adjacent to the endothelial cell or tumor cells or leukemia cells a.2) Effectors: Inhibitors of Cell Proliferation, for Example the retinoblastoma protein (pRb=p110) or the related p107 and p130 proteins The retinoblastoma protein (pRb/p110) and the related p107 and p130 proteins are inactivated by phosphorylation. Preferably, genes of these cell cycle inhibitors to be used are those which have mutations for the inactivation sites of the expressed proteins without these being impaired in their function thereby. Examples of these mutations have been described for p110.

The DNA sequence for the p107 protein or the p130 protein is mutated analogously.

The p53 protein

The protein p53 is inactivated in the cell either by binding to specific proteins, such as, for example, MDM2, or by oligomerization of the p53 by means of the dephosphorylated C-terminal serine. Preferably a DNA sequence for a p53 protein is thus used which is truncated at the C terminus by serine 392.

p21 (WAF-1)

the p16 protein other cdk inhibitors the GADD45 protein the Bak protein the Bax protein a.3) Effectors: Coagulation-inducing Factors and Angiogenesis Inhibitors, for Example:

plasminogen activator inhibitor-1 (PAI-1)

PAI-2

PAI-3 angiostatin and/or endostatin interferons (IFNα, IFNβ or IFNγ)

platelet factor 4

IL-12

TIMP-1

TIMP-2

TIMP-3 leukemia inhibitory factor (LIF)

tissue factor (TF) and its coagulation-active fragments a.4) Effectors: Cytostatic and Cytotoxic Proteins, for Example perforin granzyme

IL-2

IL-4

IL-12 interferons, such as, for example, IFN-α, IFNβ or IFNγ

TNF, such as TNFα or TNFβ oncostatin M sphingomyelinase magainin and magainin derivatives a.5) Effectors: Cytostatic or Cytotoxic Antibodies The cytostatic or cytotoxic antibodies include those directed against membrane structures of endothelial cells such as have been described, for example, by Burrows et al. (Pharmac. Ther. 64, 155 (1994)), Hughes et al., (Cancer Res. 49, 6214 (1989)) and Maruyama et al., (PNAS USA 87, 5744 (1990)). In particular, these include antibodies against the VEGF receptors.

In addition, these include cytostatic or cytotoxic antibodies directed against membrane structures on tumor cells. Antibodies of this type have been clearly described, for example, by Sedlacek et al. (Contrib. to Oncol. 32, KargerVerlag, Munich (1988) and Contrib. to Oncol. 43, Karger Verlag, Munich (1992)). Further examples are antibodies against sialyl Lewis; against peptides on tumors, which are recognized by T cells; against proteins expressed from oncogenes; against gangliosides such as GD3, GD2, GM2, 9-0-acetyl GD3, fucosyl GM1; against blood group antigens and their precursors; against antigens on the polymorphic epithelial mucin, against antigens on heat shock proteins In addition, these include antibodies directed against membrane structures of leukemia cells. A large number of monoclonal antibodies of this type have already been described for diagnostic and therapeutic procedures (reviews in Kristensen, Danish Medical Bulletin 41, 52 (1994);

Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)). Depending on the type of leukemia, suitable ligands are, for example, monoclonal antibodies or antigen-binding antibody fragments thereof directed against the following membrane antigens:

| Cells | Membrane antigen |
| --- | --- |
| AML | CD13 |
|  | CD15 |
|  | CD33 |
|  | CAMAL |
|  | Sialosyl-Le |
| B-CLL | CDS |
|  | CD1c |
|  | CD23 |
|  | Idiotypes and isotypes of the membrane immunoglobulins |
| T-CLL | CD33 |
|  | M38 |
|  | IL-2 receptors |
|  | T cell receptors |
| ALL | CALLA |
|  | CD19 |
|  | Non-Hodgkin lymphoma |

The humanization of murine antibodies, and the preparation and optimization of the genes for Fab and rec. Fv fragments is carried out according to the technique known to the person skilled in the art (Winter et al., Nature 349, 293 (1991); Hoogenbooms et al., Rev. Tr. Transfus. Hemobiol. 36, 19 (1993); Girol. Mol. Immunol. 28, 1379 (1991) or Huston et al., Intern. Rev. Immunol. 10, 195 (1993)). The fusion of the rec. Fv fragments with the component b) and/or components c) is carried out using the prior art known to the person skilled in the art by expression of a gene coding for the fusion protein.

a.6) Effectors: Inducers of Inflammation, for Example

IL-1

IL-2

RANTES (MCP-2)

monocyte chemotactic and activating factor (MCAF)

IL-8 macrophage inflammatory protein-1 (MIP-1α, -β)

neutrophil activating protein-2 (NAP-2)

IL-3

IL-5 human leukemia inhibitory factor (LIF)

IL-7

IL-11

IL-13

GM-CSF

G-CSF

M-CSF cobra venom factor (CVF) or subsequences of CVF which correspond functionally to the human complement factor C3b, i.e. which can bind to the complement factor B and, after cleavage by the factor D, are a C3 convertase the human complement factor C3 or its subsequence C3b cleavage products of the human complement factor C3, which are functionally and structurally similar to CVF bacterial proteins which activate complement or cause inflammation, such as, for example, porins of Salmonella typhimurium, clumping factors of Staphylococcus aureus, modulins, particularly of gram-negative bacteria, major outer membrane protein of Legionellae or of Haemophilus influenza type B or of Klebsiellae or M molecules of Streptococci group G.

a.7) Effectors: Enzymes for the Activation of Precursors of Cytostatics, for Example for Enzymes, which Cleave Inactive Preliminary Substances (Prodrugs) into Active Cytostatics (Drugs).

Substances of this type and the associated prodrugs and drugs in each case have already been clearly described by Deonarain et al. (Br. J. Cancer 70, 786 (1994)), Mullen (Pharmac. Ther. 63, 199 (1994) and Harris et al. (Gene Ther. 1, 170 (1994)). For example, one of the following enzymes can be used:

herpes simplex virus thymidine kinase varicella zoster virus thymidine kinase bacterial nitroreductase bacterial β-glucuronidase plant β-glucuronidase from Secale cereale human β-glucuronidase human carboxypeptidase (CB) for example CB-A of the mast cell, CB-B of the pancreas or bacterial carboxypeptidase bacterial R-lactamase bacterial cytosine deaminase human catalase or peroxidase phosphatase, in particular human alkaline phosphatase, human acidic prostate phosphatase or type 5 acidic phosphatase oxidase, in particular human lysyl oxidase or human acidic D-aminooxidase peroxidase, in particular human gluthatione peroxidase, human eosinophil peroxidase or human thyroid gland peroxidase galactosidase b) Therapy of Autoimmune Disorders and Inflammations b.1) Target Cells:

proliferating endothelial cells or macrophages and/or lymphocytes or synovial cells b.2) Effectors for the Therapy of Allergies, for Example

IFNβ

IFNγ

IL-10 antibodies or antibody fragments against IL-4 soluble IL-4 receptors

IL-12

TGFβ b.3) Effectors for Preventing the Rejection of Transplanted Organs, for Example

IL-10

TGFβ soluble IL-1 receptors soluble IL-2 receptors

IL-1 receptorantagonists soluble IL-6 receptors immunosuppressant antibodies or VH- and VL-containing fragments thereof or VH and VL fragments thereof connected by means of a linker. Immunosuppressant antibodies are, for example, antibodies specific for the T-cell receptor or its CD3 complex, against CD4 or CD8, in addition against the IL-2 receptor, IL-1 receptor or IL-4 receptor or against the adhesion molecules CD2, LFA-1, CD28 or CD40 b.4) Effectors for the Therapy of Antibody-mediated Autoimmune Disorders, for Example

TGFβ

IFNα

IFNβ

IFNγ

IL-12 soluble IL-4 receptors soluble IL-6 receptors immunosuppressant antibodies or their $V_H$ and $V_L$-containing fragments b.5) Effectors for the Therapy of Cell-mediated Autoimmune Disorders for Example

IL-6

IL-9

IL-10

IL-13

TNFα or TNFβ

IL-13 an immunosuppressant antibody or its $V_H$- and $V_L$-containing fragments b.6) Effectors: Inhibitors of Cell Proliferation, Cytostatic or Cytotoxic Proteins and Enzymes for the Activation of Precursors of Cytostatics Examples of Proteins of this Type Have Already Been Mentioned in section a.7).

b.7) Effectors for the Therapy of Arthritis

Within the meaning of the invention, effectors are selected which directly or indirectly inhibit the inflammation, for example, in the joint and/or promote the reconstitution of extracellular matrix (cartilage, connective tissue) in the joint.

These include, for example

IL-1 receptor antagonist (IL-1-RA);

IL-1-RA inhibits the binding of IL-1α, β soluble IL-1 receptor; soluble IL-1 receptor binds and inactivates IL-1

IL-6

IL-6 increases the secretion of TIMP and superoxides and decreases the secretion of IL-1 and TNFα by synovial cells and chondrocytes soluble TNF receptor soluble TNF receptor binds and inactivates TNF.

IL-4 IL-4 inhibits the formation and secretion of IL-1, TNFα and MMP

IL-10 IL-10 inhibits the formation and secretion of IL-1, TNFα and MMP and increases the secretion of TIMP insulin-like growth factor (IGF-1) IGF-1 stimulates the synthesis of extracellular matrix.

TGFβ, especially TGFβ1 and TGFβ2 TGFβ stimulates the synthesis of extracellular matrix.

superoxide dismutase

TIMP, especially TIMP-1, TIMP-2 or TIMP-3 c) Therapy of Deficient Formation of Cells of the Blood c.1) Target Cells:

proliferating, immature cells of the hematogenic system or stroma cells adjacent to the hematogenic cells c.2) Effectors for the Therapy of Anemia, for Example erythropoietin c.3) Effectors for the Therapy of Leukopenia, for Example

G-CSF

GM-CSF

M-CSF c.4) Effectors for the Therapy of Thrombocytopenia, for Example

IL-3 leukemia inhibitory factor (LIF)

IL-11 thrombopoietin d) Therapy of Damage to the Nervous System d.1) Target Cells:

glia cells or proliferating endothelial cells d.2) Effectors: Neuronal Growth Factors, for Example

FGF nerve growth factor (NGF) brain-derived neurotrophic factor (BDNF)

neurotrophin-3 (NT-3)

neurotrophin4 (NT-4)

ciliary neurotrophic factor (CNTF)

d.3) Effectors: Enzymes, for Example tyrosine hydroxylase dopa decarboxylase d.4) Effectors: Cytokines and their Inhibitors which Inhibit or Neutralize the Neurotoxic Action of TNFα, for Example

TGFβ soluble TNF receptors

TNF receptors neutralize TNFα

IL-10

IL-10 inhibits the formation of IFNγ, TNFα, IL-2 and IL4 soluble IL-1 receptors

IL-1 receptor I

IL-1 receptor II soluble IL-1 receptors neutralize the activity of IL-1

IL-1 receptor antagonist soluble IL-6 receptors e) Therapy of Disorders of the Blood Clotting and Blood Circulation System e.1) Target Cells:

endothelial cells or proliferating endothelial cells or somatic cells in the vicinity of endothelial cells and smooth muscle cells or macrophages e.2) Target Structures: Proteins of the Blood Clotting System Such as, for Example thrombin fibrin e.3) Effectors for Inhibiting Clotting or for Promoting Fibrinolysis, for Example tissue plasminogen activator (tPA)

urokinase-type plasminogen activator (uPA)

hybrids of tPA and uPA protein C hirudin serine proteinase inhibitors (serpines), such as, for example, C-1S inhibitor, α1-antitrypsin or antithrombin III tissue factor pathway inhibitor (TFPI)

e.4) Effectors for Promoting Clotting, for Example

F VIIII

F IX von Willebrand factor

F XIII

PAI-1

PAI-2 tissue factor and fragments thereof e.5) Effectors: Angiogenesis Factors, for Example

VEGF

FGF

Tie-1

Tie-2 e.6) Effectors for Lowering Blood Pressure, for Example kallikrein endothelial cell nitric oxide synthase e7) Effectors for Inhibiting the Proliferation of Smooth Muscle Cells after injuries of the endothelial layer, for example an antiproliferative, cytostatic or cytotoxic protecin or an enzyme for the cleavage of precursors of cytostatics into cytostatics as already mentioned above (section a.7)

e.8) Effectors: Further Blood Plasma Proteins, for Example

C1 inactivator serum cholinesterase transferrin 1-antritrypsin f) Vaccinations f.1) Target Cells:

muscle cells or macrophages and/or lymphocytes f.2) Effectors for the Prophylaxis of Infectious Disorders The possibilities of preparing efficacious vaccines in a conventional way are restricted.

The effector to be selected is a protein, glycoprotein or lipoprotein formed from the infectious pathogen, which leads to the neutralization and/or to the elimination of the pathogen by triggering an immune reaction, i.e. by antibody binding and/or by means of the cytotoxic T lymphocytes. So-called neutralization antigens of this type have already been used as vaccine antigens (see review in Ellis, Adv. Exp. Med. Biol. 327, 263 (1992)).

Preferably, within the meaning of the invention neutralization antigens of the following pathogens are employed:
- influenza A virus
- HIV
- rabies virus
- HSV (herpes simplex virus)
- RSV (respiratory syncytial virus)
- parainfluenza virus
- rotavirus
- VZV (varicella zoster virus)
- CMV (cytomegalovirus)
- measles virus
- HPV (human papilloma virus)
- HBV (hepatitis B virus)
- HCV (hepatitis C virus)
- HDV (hepatitis D virus)
- HEV (hepatitis E virus)
- HAV (hepatitis A virus)
- Vibrio cholera antigen
- Borrelia burgdorferi
- Helicobacter pylori
- malaria antigen
- Effectors within the meaning of the invention, however, also include an antiidiotype antibody or its antigen-binding fragments whose antigen-binding structures (the complementarity determining regions) are copies of the protein or carbohydrate structure of the neutralization antigen of the infectious pathogen.

Antiidiotype antibodies of this type can particularly replace carbohydrate antigens in infectious bacterial pathogens.

Antiidiotypic antibodies of this type and their cleavage products have been clearly described by Hawkins et al. (J. Immunother. 14, 273 (1993)) and Westerink and Apicella (Springer Seminars in Immunopathol. 15, 227 (1993)).

f.3) Effectors: Tumor Antigens

These include antigens on tumor cells. Antigens of this type have been clearly described, for example, by Sedlacek et al. (Contrib. to Oncol. 32, Karger Verlag, Munich (1988) and Contrib. to Oncol 43, Karger Verlag, Munich (1992)).

Further examples are the following antigens or, for antiidiotype antibodies, correspond to the following antigens:
- sialyl Lewis
- peptides on tumors, which are recognized by T cells
- proteins expressed by oncogenes
- blood group antigens and their precursors
- antigens on the polymorphic epithelial mucin
- antigens on heat shock proteins g) The Therapy of Chronic Infectious Diseases g.1) Target Cell:
- liver cell
- lymphocyte and/or macrophage
- epithelial cell
- endothelial cell g.2) Effectors, for Example
- a protein which has cytostatic, apoptotic or cytotoxic actions.
- an enzyme which cleaves a precursor of an antiviral or cytotoxic substance into the active substance.

g.3) Effectors: Antiviral Proteins
- antivirally active cytokines and growth factors. These include, for example, IFNα, IFNβ, IFN-γ, TNFβ, TNFα, IL-1 or TGFβ
- antibodies of a specificity which inactivates the respective virus or produces its $V_H$- and $V_L$-containing fragments or its $V_H$ and $V_L$ fragments connected by means of a linker as already described.

Antibodies against virus antigen are, for example:
- anti-HBV
- anti-HCV
- anti-HSV
- anti-HPV
- anti-HIV
- anti-EBV
- anti-HTLV
- anti-Coxsackie virus
- anti-Hantaan virus
- an Rev-binding protein. These proteins bind to the Rev RNA and inhibit Rev-dependent posttranscriptional stages of retrovirus gene expression. Examples of Rev-binding proteins are:
  RBP1-8U
  RBP1-8D
  pseudogenes of RBP1-8 g.4) Effectors: Antibacterial Proteins

The antibacterial proteins include, for example, antibodies which neutralize bacterial toxins or opsonize bacteria. For example, these include antibodies against
- Meningococci C or B
- E. coli
- Borrelia
- Pseudomonas
- *Helicobacter pylori*
- *Staphylococcus aureus* h) Combination of Identical or Different Effectors

Within the meaning of the invention, two different components d) are preferred, which have at least one additive action, to complex with one another via the components b) and c).

Within the meaning of the invention, combinations of effectors are preferred, for example, for h.1) The Therapy of Tumors
- identical or different, cytostatic, apoptotic, cytotoxic and/or inflammation-stimulating proteins or
- identical or different enzymes for the cleavage of the precursor of a cytostatic h.2) The Therapy of Autoimmune Diseases
- different cytokines or receptors having synergistic action for inhibiting the cellular and/or humoral immune reaction or
- different or identical TIMPs h.3) The Therapy of Defective Formation of Cells of the Blood
- different, hierarchically consecutive cytokines, such as, for example, IL-1, IL-3, IL-6 or GM-CSF and erythropoietin, G-CSF or thrombopoietin h.4) The Therapy of Nerve Cell Damage
- a neuronal growth factor and a cytokine or the inhibitor of a cytokine h.5) The Therapy of Disorders of the Blood Clotting and Blood Circulation System
- an antithrombotic and a fibrinolytic (e.g. tPA or uPA) or
- a cytostatic, apoptotic or cytotoxic protein and an antithrombotic or a fibrinolytic
- several different, synergistically acting blood clotting factors, for example F VIII and vWF or F VIII and F IX h.6) Vaccinations
- an antigen and an immunostimulating cytokine, such as, for example, IL-1α, IL-1β, IL-2, GM-CSF, IL-3 or IL-4 receptor
- different antigens of an infectious pathogen or different infectious pathogens or
- different antigens of a tumor type or different tumor types h.7) Therapy of Viral Infectious Diseases
- an antiviral protein and a cytostatic, apoptotic or cytotoxic protein
- antibodies against different surface antigens of a virus or several viruses h.8) Therapy of Bacterial Infectious Diseases
- antibodies against different surface antigens and/or toxins of a microorganism

Multifunction Ligand for Viral and Nonviral Vectors for Gene Therapy

Multifunctional ligands have already been described in detail in the patent application EP-A 0 846 772. Reference is made expressly to this patent application.

In the case of use as a multifunctional ligand, a component a) is to be selected which is directed against a cellular target structure. Examples of ligands (component a) specific for cellular target structures have already been mentioned in section 3).

In a multifunctional ligand, the effector (component d) is selected such that it binds to a viral vector or to a nonviral vector. Effectors of this type are, for example:
- a cell receptor for a virus, such as, for example, for AdV, AAV, a lentivirus, an RTV, vaccinia virus, HSV, influenza virus, HJV
- a recombinant antibody specific for a virus protein, for a nonviral vector or for a nucleic acid, such as, for example, an IgG, F(ab)$_2$, Fab, rec. Fv, diabody or single-chain, double antigen-binding protein
- a peptide having a reactive group for conjugation to a virus protein
- a peptide having binding affinity for a defined nucleic acid sequence Preferentially, the component d) is a complete antibody molecule or an epitope-binding fragment of a human antibody.

The murine monoclonal antibodies are preferably employed in humanized form. Humanization is carried out in the manner presented by Winter et al. (Nature 349, 293 (1991)) and Hoogenboom et al. (Rev. Tr. Transfus. Hemobiol. 36, 19 (1993)). Antibody fragments and recombinant Fv fragments are prepared according to the prior art, and as already described.

Whether a bivalent or a monovalent fragment is used is dependent on the choice of the antibody specificity and of the gene construct. If the selected antibody adversely affects the fusion activity of the coat protein of a viral gene construct (as described, for example, by Ubol et al. (J. Virol. 69 1990 (1995)), a monovalent antibody fragment is to be preferred.

The specificity of the antibody depends on the type of gene construct used.

If the gene construct is a naked RNA or a naked DNA on its own or as a complex with a nonviral carrier, one of the embodiments according to the invention of this invention is that the specificity of the antibody is directed against those epitopes which have been introduced into the DNA.

Epitopes of this type can be produced by binding of xenogenic substances to the DNA. Examples of these are
- crosslinkages of the DNA by cisplatin
- alkylation on the $N^7$ of guanine by alkylating agents such as nitrogen mustard, melphalan, chlorambucil
- intercalation into the double helix of the DNA of anthracyclines such as doxorubicin, daunomycin Monoclonal antibodies against newly introduced epitopes on the DNA of this type are, for example:
- antibodies against methylated DNA
- antibodies againt $O^6$-ethyl deoxyguanosine (after treatment of the DNA with ethyinitrosourea)
- antibodies against $N^7$-ethylguanine
- antibodies against $N^5$-methyl-$N^5$-formyl-2,5,6 triamino-4-hydroxypyrimidine
- antibodies against $O^6$-methyl-2'-deoxyguanosine
  - $O^6$-ethyl-2'-deoxyguanosine
  - $O^6$-n-butyl-2'-deoxyguanosine
  - $O^6$-isopropyl-2'-deoxyguanosine
  - $O^4$-methyl-2'-deoxythymidine
  - $O^4$-ethyl-2'-deoxythymidine
- antibodies against melphalan adducts with DNA
- antibodies against anthracyclines Novel epitopes in the DNA also result, however, due to methylation of the DNA during the course of DNA metabolism.

It is known of a number of E. coli strains that they methylate the DNA of the plasmids introduced into them on the $N^6$ of adenine (Winnacker, From Genes to Clones, page 18/19, VCH Publisher, Weinheim (1987)). Bacteria have the enzyme DNA-adenine methylase, which specifically methylates adenine on the $N^6$ position during replication (Hattman et al., J. Mol. Biol. 126, 367 (1978)).

This invention thus relates particularly to the use of the monoclonal antibodies against methylated DNA
- in particular against methylated $N^6$ of adenine—in the ligand system according to the invention.

If the gene construct is in a complex with a nonviral carrier, a further particular embodiment of this invention is that the specificity of the antibody is directed against an epitope on the carrier.

These carriers include cationic polymers, peptides, proteins, polyamides or cationic lipids such as, for example, cationic lipids and phospholipids. Examples of antibodies against carriers of this type are
- antibodies against spermidine, spermine or putrescine
- antibodies against polylysine
- antibodies against albumin
- antibodies against phospholipid
- antibodies against polyethyleneimine If the gene construct is a virus, the specificity of the antibody is directed against one or more identical or different epitopes on the coat protein of the virus. Since the linker in the ligand system used is preferentially a fusogenic peptide or protein, antibodies can also be used which adversely affect the cell adhesion and/or the fusiogenic activity of the virus by binding to the coat protein.

Antibodies against coat proteins of viruses which can be used as vectors are, for example, antibodies against the murine leukemia virus HIV virus adenovirus herpes simplex virus cytomegalovirus minute virus of mice adeno-associated virus Sindbis virus vaccinia virus In a further preferred embodiment of the invention, the component d) is the cell-external portion of an Fc receptor. One of the antibodies already mentioned, which binds directly or indirectly to the gene construct with its antigen-binding portion, binds to this Fc receptor via its Fc portion.

In a further preferred embodiment, the component d) is a cationic structural unit, such as, for example, a cationic amino acid, a cationic peptide or protein or a biogenic amine, which can complex with the gene construct.

These cationic structural units include, for example:

lysine or polylysine arginine or polyarginine histidine or polyhistidine peptides comprising at least 1 lysine, 1 arginine and/or 1 histidine polyamines such as, for example, cadaverine, spermidine, spermine, agmatine or putrescine In a further preferred embodiment, the component d) is the receptor for the coat protein of the virus harboring the transgene.

Receptors of this type have been described, for example, for the following viruses:

HIV the CD4 molecule (soluble or native)

galactosylceramide receptors for chemokines

HBV the IL-6 receptor annexin or apolipoprotein

HTLV the IL-2 receptor (the β and the γ chain)

measles virus the CD46 molecule

Friend leukemia virus the erythropoietin receptor varicella zoster the Fc fragment of human immunglobulin G Sendai virus glycophorin influenza C virus N-acetyl-9-acetamido-9-deoxyneuraminic acid 9-O-acetyl-N-acetylneuraminic acid foot and mouth disease virus integrin αVβ3

EBV complement receptor 2 (CD21)

herpes simplex virus the 275 kDa mannose-6-phosphate receptor or the 46 kDa mannose-6-phosphate receptor adenoviral virus CAR (Coxsackie adenovirus receptor)

Insertion of a Fusogenic Peptide or of a Translocalization Peptide

In the case of multivalent protein complexes in which the effector (component d) has to penetrate intracellularly in order to act prophylactically or therapeutically or which, as a multifunctional ligand, is to insert a vector into the cytoplasm of a cell, a fusogenic peptide is to be attached to the effector. This fusogenic peptide can be inserted between the components c) and d) or attached to the component d). The fusogenic peptides include, for example:

peptides comprising the translocation domain (domain II) of the exotoxin A of Pseudomonas peptides comprising the peptide GLFEALLELLESL-WELLLEA (SEQ ID NO.: 1)

peptides comprising the peptide ADLAEA[LAEA]$_4$LAAAAGC (SEQ ID NO.: 2)

peptides comprising the peptide FAGV-VLAGAALGVAAAAQI (SEQ ID NO.: 3) of the fusion protein of the measles virus peptides comprising the peptide GLFGAIAGFIEGGW-WGMIDG (SEQ ID NO.: 4) of the HA2 protein of influenza A peptides comprising the peptide GLFGAIAGFIENG-WEGMIDGGLFGAIAGFIENGWEGMIDG (SEQ ID NO.: 5) or the peptide

GLFGAIAGFIE; (SEQ ID NO.: 6)

ALFGAIAGFIE; (SEQ ID NO.: 7)

LFLGAIAGFIE; (SEQ ID NO.: 8)

LLLGAIAGFIE; (SEQ ID NO.: 9)

LILGAIAGFIE; (SEQ ID NO.: 10)

GIFGAIAGFIE; (SEQIDNO.: 11)

GLLGAIAGFIE; (SEQ ID NO.: 12)

GLFAAIAGFIE; (SEQ ID NO.: 13)

GLFEAIAGFIE; (SEQ ID NO.: 14)

GLFGAMAGFIE; (SEQ ID NO.: 15)

GLFGAIAGLIE; (SEQ ID NO.: 16)

GLFGAIAGFIV; (SEQ ID NO.: 17)

GLFEAIAEFIEGGWEGLIEG (SEQ ID NO.: 18) or

GLLEALAELLEGGWEGLLEG (SEQ ID NO.: 19).

In the context of the present invention, proteins of viruses are additionally used which have fusiogenic properties. A number of viruses have fusiogenic and/or translocating coat proteins, for example paramyxoviruses, retroviruses and herpes viruses. These include, for example, the TAT protein of HIV or its translocalizing amino acid sequence or the VP22 protein of HSV.

A number of viruses additionally have glycoproteins which are responsible both for virus attachment and subsequently for cell membrane fusion (Gaudin et al., J. Gen. Viro. 76, 1541 (1995)).

Proteins of this type are formed, for example, from alpha-, rhabdo- and orthomyxoviruses.

Viral fusogenic proteins within the meaning of the invention have been clearly described by Hughson (Curr. Biol. 5, 265 (1995)), Hoekstra (J. Bioenergetics Biomembranes 22, 675 (1990)), and White (Ann. Rev. Physiol. 52, 675 (1990)).

Fusogenic proteins within the meaning of this invention are, for example:

the hemagglutinin of influenza A or B viruses, in particular the HA2 component the M2 protein of influenza A viruses employed on its own or in combination with the hemagglutinin of influenza virus or with mutants of neuraminidase of influenza A, which lack enzyme activity, but which bring about hemagglutination.

Peptide analogs of the influenza virus hemagglutinin the HEF protein of the influenza C virus The fusion activity of the HEF protein is activated by cleavage of the HEFo into the subunits HEF1 and HEF2.

the transmembrane glycoprotein of filoviruses, such as, for example
the Marburg virus
the Ebola virus the transmembrane glycoprotein of the rabies virus the transmembrane glycoprotein (G) of the vesicular stomatitis virus the fusion protein of the HIV virus, in particular the gp41 component and fusogenic components thereof the fusion protein of the Sendai virus, in particular the amino-terminal 33 amino acids of the F1 component the transmembrane glycoprotein of the Semliki forest virus, in particular the E1 component the transmembrane glycoprotein of the tickborn encephalitis virus the fusion protein of the human respiratory syncytial virus (RSV) (in particular the gp37 component)

the fusion protein (S protein) of the hepatitis B virus the fusion protein of the measles virus the fusion protein of the Newcastle disease virus the fusion protein of the visna virus the fusion protein of murine leukemia virus (in particular p15E)

the fusion protein of the HTL virus (in particular gp21)

the fusion protein of the simian immunodeficiency virus (SIV)

Viral fusogenic proteins are obtained either by dissolving the coat proteins of a virus concentration with the aid of detergents (such as, for example, β-D-octylglucopyranoside) and separation by centrifugation (review in Mannio et al., BioTechniques 6, 682 (1988)) or else with the aid of molecular biology methods known to the person skilled in the art.

Insertion of Protease Cleavage Sequences

The invention additionally relates to multifunctional protein complexes which, between the components a) and b) or between the components c) and d), have a peptide sequence which is cleavable by proteases. By means of these proteases, the effector can be cleaved from the ligand (component a) or from the ligand and the mutated proteins [components a), b) and c)] and, for example, can display its action in free form at the site of the concentration of the multivalent protein complexes.

The invention relates in paticular to cleavage sequences which are cleaved by proteases which are formed in tumors or by tumor cells or by inflammatory cells.

Examples of Cleavage Sequences for the Enzymes
plasminogen activator
prostate-specific antigen
cathepsin
stromelysin
collagenase and plasminogen are listed in the patent application EP-A 0 859 058, to which reference is expressly made.

The invention additionally relates to multivalent protein complexes having cleavage sequences which are cleaved by proteases which are formed by viruses.

Examples of cleavage sequences for enzymes of retroviruses, polio viruses, influenza viruses, Epstein-Barr viruses, herpes simplex viruses, hepatitis viruses, pox viruses, cytomegaloviruses and dengue viruses are listed in German patent application DE 198 50987.1 (not published), to which reference is expressly made.

The invention additionally relates to multivalent protein complexes having cleavage sequences which are cleaved by proteases which can be released in the cell.

Examples of proteases of this type are, for example, caspases, such as caspases 1, 2, 3, 4, 5, 6, 7, 8 and 9.

The associated cleavage sequences are listed in the patent application DE 198 50987.1 (not published), to which reference is expressly made.

Synthetic Transcription Factors for Controlling the Expression of Genes

Activator responsive promoters have been described in the patent application EP-A 0 805 209. In this invention, reference is expressly made to this invention. These activator-responsive promoters are activated by a synthetic transcription factor, which in principle consists of two activator subunits, the subunit A and the subunit B. Both subunits contain binding proteins (A, B). In EP-A 0 805 209, binding proteins (A, B) were selected which naturally form the complex AB, such that the subunit A is joined to the subunit B to give a functional transcription factor complex. The invention now relates to synthetic transcription factors for activator-responsive promoters, in which the binding proteins A+B are mutated binding proteins.

In the simplest form, this synthetic transcription factor complex consists of the following components:

Component a) at least one ligand for a reaction partner =activation domain

Component b) a binding protein mutated such that it exclusively links to the component c)

Component c) a binding protein mutated such that it exclusively links to the component b)

Component d) at least one effector=a DNA-binding domain

The invention additionally relates to nucleic acid constructs which code for a transcription factor complex according to this invention. The expression of this nucleic acid construct is in this under the control of promoters such as listed in the patent application EP-A 0 805 209, to which reference is expressly made.

Novel Analytical and Diagnostic Systems

The invention relates to novel complex-forming proteins for analytical or diagnostic systems for the qualitative or quantitative analysis or diagnosis of a reactant.

In such diagnostic systems, the component a) is at least one ligand which enters into a specific binding with the reactant to be analyzed. This ligand is directly or indirectly linked to at least one mutated binding protein [components b)1-b)n], such that the component ab results. In addition, at least one mutated binding protein [component c)1-c)n], which can dimerize with the component b) by means of at least two binding sites, is linked to at least one effector (component d), where this effector is a signal-emitting substance (analyte). The component cd results from the combination of the component c) with the component d).

The component ab binds via a) to the reactant. By means of complex formation of the component ab with the component cd, the amount of reactant to which the component ab is bonded via component a) can be determined.

Figure 1A:
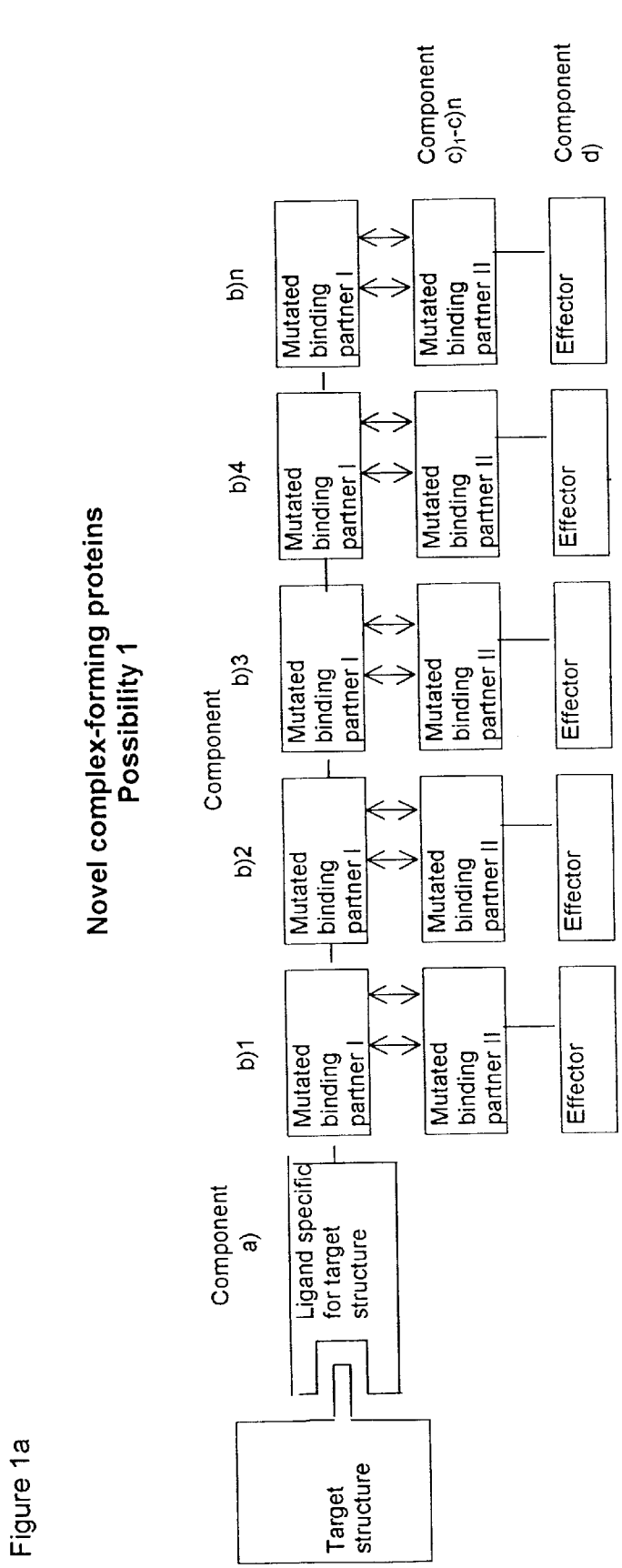
FIG. 1: (*a*) Schematic representation of the novel complex-forming proteins, possibility 1

This diagnostic system can, for example, be used in the two embodiments shown (see FIGS. 1 and 2):

In the first embodiment (see FIG. 1), the component b) is a homo- (or hetero)multimer [component b)1-b)n], to which many identical (or different) components c) bind, in each case as monomers and in each case linked to the component d).

Using this embodiment, many signal-emitting components [analytes, component d)] are bound to the reactant to be analyzed, which increases the sensitivity of the system.

In the second embodiment (see FIG. 2) both the component b) and the component c) are multimers, only one or a few components d) being bound to the component c). With this embodiment, although only a few components d) are bound to the reactant to be analyzed, the binding between the components c) and d) is extremely strong, which can increase the specificity of the detection of the reactant to be analyzed.

Figure 1B:
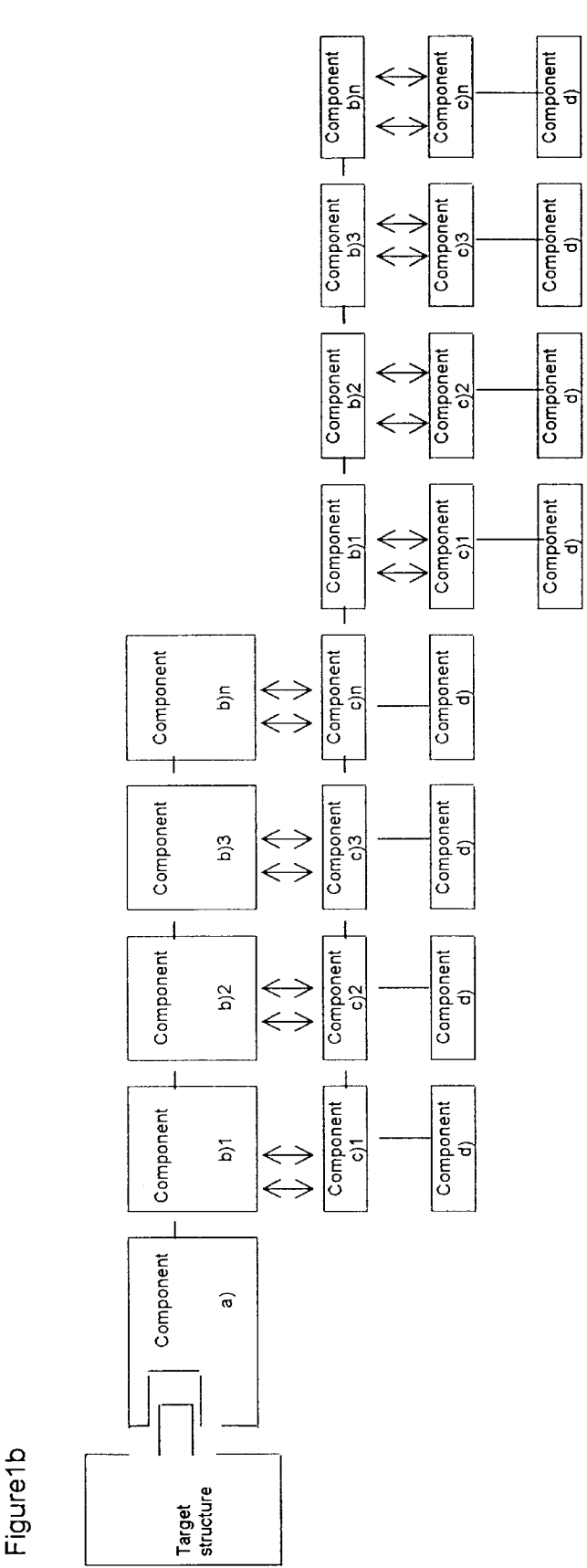

In a further particular embodiment of the invention, the components c) [$c_1$-cn] is bound to at least one further component b [$b_1$–bn], to which at least one further component cd can dimerize. An example of this is shown in FIG. 1b.

This particular embodiment increases the sensitivity of the test system considerably.

With the aid of this analytical or diagnostic system according to the invention, a reactant can be determined in or on a solid phase, in a fluid, for example in a body fluid, on cells and in tissues.

As used above, "a reactant" refers to a molecule whose detection is desired. A reactant in this embodiment binds to component a) and is for example, a molecule that binds to one or more molecules listed as representative of component a) in the present embodiment.

According to the invention, the component a) can be:
- a nucleotide sequence. If a nucleotide sequence is chosen, this is to be derivatized terminally for example according to WO95/02422 or by insertion of a binding sequence for a nucleotide binding protein (such as, for example, for LexA, Gal4 or for a transcription factor) or for an antibody such that the component b) can be coupled to it directly or indirectly via a nucleotide-binding protein or via an antigen-binding portion of an antibody.
- a ligand for a cell receptor
- a virus coat protein
- a cell receptor for a virus coat protein
- a cell receptor for a growth factor, a cytokine, a chemokine, a peptide hormone, a mediator or a steroid
- a protein which links to a partner protein and thereby takes part in a biological reaction chain, for example a complement factor, a clotting factor, a factor of the kinin system, of the fibrinolysis system or a plasmatic or cell enzyme inhibitor or a plasmatic or cell enzyme
- the extracellular portion of an Fc receptor, to which an antibody specific for a target cell is bound via its Fc portion
- an antibody molecule or the epitope-binding portion of a murine or human antibody molecule.

Recombinant antibody fragments are prepared as already mentioned in section 3).

In an analytical or diagnostic system according to the invention, the signal-emitting component, the analyte (component d), for example, can be a fluorescent molecule, a molecule which causes a chemoluminescence reaction, an enzyme, such as, for example, a phosphatase or peroxidase for the cleavage of a substrate to be measured, an isotope or a metal.

With the aid of the analytical and diagnostic system according to the invention, a reactant to be determined is mixed with an excess of the component. The fraction of component ab not bound to the reactant to be determined is removed, for example by washing. Subsequently, the component bound to the reactant is treated with an excess of component cd, the fraction of the component bc not bound to the component ab is removed, for example by washing, and the component d) bound to the reactant via the components ab and c) is determined.

EXAMPLES

Preparation and Testing of an Activator-responsive Promoter Unit

An activator-responsive promoter unit was prepared in which an activator subunit A is linked to an activator subunit B (see FIG. 3). The combination is carried out by means of mutated c-jun and mutated c-fos (see FIG. 4). The complex is a transcription factor which activates an actvator-responsive promoter.

An embodiment of the activator component of the activator-responsive promoter unit according to the invention consists, downstream in succession, of the following different nucleotide sequences:

Activator Subunit A:
- the promoter of the cyclin A gene (nucleic acids −214 to +100; Zwicker et al., EMBO J. 14, 4514 (1995))
- the nuclear localization signal (NLS) of SV40 (SV40 large T, amino acids 126–132; PKKKRKV (SEQ ID NO.: 20), Dingwall et al., TIBS 16, 478 (1991))
- the acidic transactivation domain (TAD) of HSV-1 VP16 (VP16, amino acids 411 to 455; Triezenberg et al., Genes Dev. 2, 718 (1988))
- the cDNA for the leucine zipper part of the c-jun protein (amino acids 276 to 312; Mark et al., Nature 373, 257 (1995)) in which the amino acids 283, 288 and 302 are mutated (m-jun).

Description of the Mutations (FIG. 4):
Amino acid 283 K→E
Amino acid 288 K→E
Amino acid 302 R→E Activator Subunit B:
- the promoter of the tyrosinase gene (2X the enhancer sequence, nucleic acids −2014 to −1820 and the nuclear promoter nucleic acids −209 to +51; Shibata et al., J. Biol: Chem. 267, 20584 (1992))
- the nuclear localization signal (NLS) of SV40 (SV40 large T, amino acids 126–132; PKKKRKV (SEQ ID NO.: 20), Dingwall et al., TIBS 16, 478 (1991))
- the cDNA for the DNA-binding domain of the Gal4 protein (amino acids 1 to 147, Chasman und Kornberg, Mol. Cell. Biol. 10, 2916 (1990))
- the cDNA for the leucine zipper part of the c-fos proteins (amino acids 160 to 196; Mark et al., Nature 373, 257 (1995)) in which the amino acids 167, 172 and 181 are mutated (m-fos).

Description of the Mutations (FIG. 4):

Amino acid 167 E→K

Amino acid 172 E→K

Amino acid 181 E→K

Dimerization of Mutated c-fos with Mutated c-jun

The expression products of the activator subunits A and B dimerize by binding of the mutated c-fos leucine zipper to the mutated c-jun leucine zipper.

The dimerization of the activator subunits A and B, i.e. the binding of the mutated c-fos leucine zipper to the mutated cjun leucine zipper, was tested as follows:

The proteins were synthesized in an in vitro translation system (TNT T7 quick coupled transcription/translation system, Promega, Madison, Wis.) with or without ($S^{35}$)-methionine. Subsequently, the synthesized proteins (m-jun-VP16 and m-fos-Gal4) were mixed in the ratio 1:1 and the complex was separated by gel electrophoresis and, after immunoprecipitation, analyzed with an anti-GAL4 antibody.

The following results were obtained:

The protein m-jun-VP16 can be linked to the protein m-fos-GAL4.

The protein m-jun-VP16 cannot be linked to the protein wt-fos-GAL4 and the protein wt-jun-VP16 cannot be linked to the protein m-fos-GAL4 (see Table 1).

The dimeric protein is a chimeric transcription factor for the activator-responsive promoter 10× (Gal4-SV40).

Activator-responsive promoter and the effector system

The activator-responsive promoter has the following composition:

10× the binding sequence for Gal4-binding protein having the nucleotide sequence 5'-CGGAGTACTGTCCTCCG-3' (Webster et al., Cell 52, 169 (1988); SEQ ID NO.:21)

the basal promoter of SV40 (nucleic acids 48 to 5191; Tooze (Ed). DNA Tumor Viruses (Cold Spring Harbor, New York, Cold Spring Harbor Laboratory))

the cDNA for the reporter gene luciferase (Luc) (Nordeen, BioTechniques 6, 454 (1988))

The order of the nucleotide sequences and their activation units is shown in FIG. 5.

The nucleotide construct prepared in this way is cloned into the pGL3 plasmid vector (Promega; Madison, USA) which is employed directly or in colloidal dispersion systems for an in vivo application.

The functioning of the complete activator-responsive promoter unit is as follows:

The promoter cyclin A regulates, in a cell cycle-specific manner, the transcription of the combined cDNAs for the activation domain of VP16 and the mutated leucine zipper of c-jun (activation subunit A) (FIG. 3)

The promoter tyrosinase restricts the transcription of the combined cDNAs for the Gal4 binding domain, the NLS of SV40 and the mutated leucine zipper of c-fos on melanoma cells (activation subunit B) (FIG. 3).

The dimeric protein is a chimeric transcription factor for the activator-responsive promoter (DNA sequence for the Gal4-binding domain/SV40 promoter) and for the transcription of the effector gene (=reporter gene=luciferase gene) (FIG. 5).

The Preparation of the Construct

The linkage of the individual constituents of the construct and insertion into a plasmid (pGL3, Promega, Madison Wis. USA) (FIG. 6) is carried out via suitable restriction sites which are included on the termini of the various elements by means of PCR amplification. The linkage is carried out with the aid of enzymes which are specific for the restriction sites and known to the person skilled in the art and DNA ligases. These enzymes can be obtained commercially.

Using the plasmids described, tumor cells held in culture (MeWo: human melanoma cells, PC3: human prostate cells) are transfected using the DOTAP method known to the person skilled in the art (Boehringer Mannheim, Indianapolis, Ind.) and the amount of luciferase produced from the cells is measured (Herber et al., Oncogene 9, 1295 (1994); Lucibello et al., EMBO J. 14, 132 (1995) and Jérôme et al., Hum. Gen. Ther., in print (1998)).

To check the cell cycle specificity, the tumor cells are synchronized in G0/G1 over 48 hours by withdrawal of methionine. BrdU incorporation shows that MeWo and PC3 cells can be synchronized after methionine withdrawal (Jerome et al., Hum. Gen. Ther., in press (1998)).

Results

The following results are obtained: in transfected MeWo and PC3 cells, a distinct increase in the luciferase in comparison with nontransfected tumor cells can be determined (Tables 2 and 3).

Proliferating MeWo (DNA>2S) form distinctly more luciferase than tumor cells (DNA=2S) synchronized in G0/G1 and than proliferating PC3 cells (Tables 2 and 3).

The activator subunits A and B, which contain mutated leucine zipper, cannot bind to the endogenous c-fos and c-jun (Table 2).

The activator subunits A and B, which contain mutated leucine zipper, are more active than the system with CD4 and LCK (Table 2), described in detail in the patent application EP-A 0 805 209, due to the strong binding of the mutated c-fos leucine zipper to the mutated c-jun leucine zipper.

Thus the activator-responsive promoter unit leads to a cell-specific, cell cycle-dependent expression of the gene luciferase (Table 4).

Further Results with the Fos/jun System

The activity of the novel complex-forming protein in melanoma and lung carcinoma xenotransplants Melanoma xenotransplants were incorporated into nude mice by interadermal injection of $10^6$ MeWo cells.

Lung carcinoma xenotransplants were incorporated into nude mice by subcutaneous injection of $2.10^7$ H322 cells (H3 22, bronchoalveolar carcinoma, human ATCC No. CRL 5806).

When the xenotransplants reached a size of 4 mm, they were coinjected intratumorally with the following plasmid combination in a carrier solution of 5% glucose, 0.01% Triton X100.

Plasmid combination:

6 ng of the pRL-SV40 vector (Promega Incorporated)+30 µg of the pGL3 promoter vector (Promega Incorporated)

6 ng of the pRL-SV40 vector (Promega Incorporated) +15 µg of 10×BS Gal4-SV40-luc+15 µg of the Tyr-m-fos-CycA-VP16

6 ng of the pRL-SV40 vector (Promega Incorporated)+15 µg of 10×BS Gal4-SV40-luc+15 µg of Tyr-m-fos-CycA-VP16-m-jun.

All these plasmids were isolated using the endofree QIAGEN plasmid Maxi Kit (QIAGEN Inc.).

The pRL-SV40 vector was used as an internal control in order to standardize the results of the various xenotransplants.

24 h after the injection, the mice were killed, the tumors were dissected out and mechanically comminuted, and the luciferase activity in the lysate was measured with the aid of the dual luciferase reporter gene assay system (Promega Incorporated). The results were indicated as the ratio of the glowworm luciferase activity to the pRL-SV40 activity and translated to the protein concentration.

Results (see Table 5)

1. In both types of xenotransplants, the melanoma and the lung carcinoma xenotransplants, the constitutively expressed promoter SV40 (pGL3 promoter construct) leads to the detection of the glowworm luciferase activity.
2. In both types of xenotransplant, no glowworm luciferage activity was found after the injection of 15 μg of 10×BS Gal4-SV40-luc+15 pg of Tyr-m-fos-CycA-VP16.
3. Glowworm luciferase activity was only found in melanoma xenotransplants after the injection of 15 μg of 10×BS Gal4-SV40-luc+15 μg of Tyr-m-fos-CycA-VP16-m-jun. This shows that the fos-jun system brings about a selective expression of the luciferase activity in the melanoma xenotransplant.

The expression of an effector gene, which is controlled by the fos/jun system, has a biological effect.

For the analysis of the ability of the fos/jun system to cause a biological action, the reporter gene luciferase was replaced by Bax cDNA (Oltvai et al., 1993). In order to be able to analyze the transfected cells, the cells were cotransfected with CMV-Iuc. A large amount of luciferase was constitutively expressed, which is easily measurable using a luciferase assay, so that the percentage of the surviving transfected cells can be calculated.

The MeWo (human melanoma) and the H322 (bronchoalveolar lung carcinoma) cell lines were transfected, as described by the manufacturer, with lipofectin (Gibco BRL Inc.) or DOTAP (Boehringer Mannheim Inc.). The cells were cotransfected with the following plasmids:

pCDNA3 (Invitrogen Inc.; control): 1 ng of CMV -luc+1 μg of Tyr-m-fos-CycA-VP16+1 μg of pCDNA3

CMV-bax (Bax cDNA, cloned in pCDNA3): 1 ng of CMV-luc+1 μg of Tyr-m-fos-CycA-VP16-m-jun+1 μg of CMV-bax pBax (control): 1 ng of CMV-luc+1 μg of Tyr-m-fos-CycA-VP16+1 μg of pBax 10×BS Gal4-SV40-bax: 1 ng of CMV-luc+1 μg of Tyr-m-fos-CycA-VP16-m-jun+1 μg of 10×BS Gal4-SV40-bax.

The luciferase values measured in the case of the cotransfection with pCDNA3 and pBax (control plasmids which expressed no Bax cDNA) were assumed to be 100% survival of the transfected cells.

48 h after the transfection, the cells were collected and the luciferase activity was measured.

Results (see Table 6)

1. If the Bax cDNA was controlled by the constitutive CMV promoter, the percentage of the surviving transfected cells in both cell types decreased, to 9–10% in MeWo cells and to 32–36% in H322 cells.
2. If the Bax cDNA was controlled by the 10×BS Gal4-SV40 promoter, the percentage of the surviving transfected cells was 100% if the Me Wo cells were cotransfected with the control plasmid (Tyr-m—fos-CycA-VP16) and decreased to 36% if Tyr-m-fos-CycA-VP16-m-jun was used. In the H3 22 cells, in both cases the percentage of the surviving transfected cells was 100%.

These results show that the activation of the fos-jun system in melanomas suffices to cause a biological effect (cell destruction) which is not to be found in non melanoma cells.

Selective expression of the fos-jun system in melanomas after the transfer of the adenovirus The Tyr-m-fos-CycA-VP16, Tyr-m-fos-CycA-VP16-m-jun and the 10×BS Gal4-SV40-luc transcription cassettes were cloned in a human E1/E3-deleted adenovirus (serotype 5) by means of bacterial recombination, as described by He et al. (1998).

The MeWo and H322 cells were coinfected for 6 hours either with

AdTyr-m-fos-CycA-VP16+Ad10×BS Gal4-SV40-luc or with

AdTyr-m-fos-CycA-VP16-m-jun+Ad10×BS Gal4-SV40-luc, and the luciferase activity was measured 48 h after the infection. The activities in both cell lines were compared with the results which were obtained with AdSV40-luc (human E1/E3-deleted adenovirus (serotype 5) using an SV40 promoter (−138/+45), D. M. Nettelbeck, unpublished data).

Results (see Table 7)

In both cell lines, the coinfection with the control adenovirus (AdTyr-m-fos-CycA-VP16) led to a weak expression of the luciferase activity, while a high activity, which was 70 times that with AdSV40-luc, was only found in MeWo cells after infection with AdTyr-m-fos-CycA-VP16-m-jun.

The selective expression of the fos-jun system in melanomas is maintained after the transfer of the fos-jun system to an adenovirus vector.

TABLE 1

| Protein-protein interaction after immunoprecipitation | | |
|---|---|---|
| (S35)-Methionine-labeled proteins | Nonradioactive proteins | Interaction ability |
| Activation domain of VP16 | wt-fos-Gal4 | − |
| wt-jun-VP16 | wt-fos-Gal4 | +++ |
| m-jun-VP16 | wt-fos-Gal4 | − |
| VP16 | m-fos-Gal4 | − |
| wt-jun-VP16 | m-fos-Gal4 | − |
| m-jun-VP16 | m-fos-Gal4 | ++++ |

TABLE 2

Luciferase activities in MeWo cells

| (Activator-responsive) promoters in the pGL-3 plasmid | Activator subunits in the pGL3 plasmid | Luciferase values (RLU) G0/G1-synchronized cells | proliferating cells |
|---|---|---|---|
| – | – | 185 | 210 |
| SV40 | – | 6240 | 28416 |
| CycA | – | 4312 | 223743 |
| Tyrp | – | 149104 | 719672 |
| 10x BS Gal4-SV40 + Tyr-m-fos-Gal4 | CycA-VP16 | 163 | 382 |
| 10xBS Gal4-SV40 + Tyr-m-fos-Gal4 | CycA-m-jun-VP16 | 271 | 18324 |
| 10xBS Gal4-SV40 + Tyr-m-fos-Gal4 | CycA-wt-jun-VP16 | 283 | 284 |
| 10xBS Gal4-SV40 + Tyr-wt-fos-Gal4 | CycA-m-jun-VP16 | 224 | 290 |
| 10xBS Gal4-SV40 | Tyr-m-fos-CycA-VP16 | 1103 | 9445 |
| 10xBS Gal4-SV40 | Tyr-m-fos-CycA-m-jun | 12665 | 1019337 |
| 10xBS Gal4-SV40 | Tyr-LCK-Gal4-CycA-VP16 | 4283 | 4997 |
| 10xBS Gal4-SV40 | Tyr-LCK-Gal4-CycACD4-VP16 | 5994 | 72435 |

TABLE 3

Luciferase activities in PC3 cells

| (Activator-responsive) promoters in the PGL3 plasmid | Activator subunits in the PGL3 plasmid | Luciferase values (RLU) G0/G1-synchronized cells | Proliferating cells |
|---|---|---|---|
| – | – | 1393 | 2114 |
| SV40 | – | 27458 | 40818 |
| CycA | – | 5835 | 131615 |
| 10x BS Gal4-SV40 | Tyr-m-fos-CycA-VP16 | 4097 | 6293 |
| 10x BS Gal4-SV40 Tyr-m-fos-Gal4- | | 8820 | 11556 |
| CycA-m-jun-VP16 | | | |

TABLE 4

Cell-specific, cell cycle-dependent expression of the luciferase gene

| Transfected plasmids (Activator-responsive) promoters in the pGL3 plasmid | Activator subunits in the pGL3 plasmid | RLU ratio (proliferating against synchronized cells) MeWo melanoma | PC3 prostate carcinoma |
|---|---|---|---|
| – | – | 0.25 | 1 |
| SV40 | | 1 | 1 |
| CycA | | 11.4 | 15.2 |
| Tyrp | | 1.1 | n.d. |
| 10xBS Gal4-SV40 + Tyr-m-fos-Gal4 | CycA-VP16 | 0.5 | 1 |
| 10xBS Gal4-SV40 + Tyr-m-fos-Gal4 | CycA-m-jun-VP16 | 14.8 | 0.9 |
| 10xBS Gal4-SV40 + Tyr-m-fos-Gal4 | CycA-wt-jun-VP16 | 0.22 | n.d. |
| 10xBS Gal4-SV40 + Tyr-wt-fos-Gal4 | CycA-m-jun-VP16 | 0.3 | n.d. |
| 10xBS Gal4-5V40 | Tyr-m-fos-CycA-VP16 | 1.9 | 1 |
| 10xBS Gal4-SV40 | Tyr-m-fos-Gal4-CycA-m-jun-VP16 | 17.7 | 0.9 |
| 10xBS Gal4-5V40 | Tyr-LCK-Gal4-CycA-VP16 | 0.26 | 1.2 |
| 10xBS Gal4-5V40 | Tyr-LCK-Gal4-CycA-CD4-VP16 | 2.6 | 1.7 |

TABLE 5

Luciferase activities in melanoma and lung carcinoma xenotransplants

| Internal control plasmid | Promoter in pGL3 activator) | Activator subunits in pGL3 | Ratio (glowworm luciferase/pRL-SV40)/mg of protein Melanoma xenotransplant | Lung carcinoma xenotransplant |
|---|---|---|---|---|
| pRL-SV40 | SV40 | | 10.9 ± 3.6 | 5.1 ± 0.4 |
| pRL-SV40 | 10xBS Gal4-SV40 | Tyr-m-fos-CycA-VP16 | 0.5 ± 0.3 | 0.017 ± 0.005 |
| pRL-SV40 | 10xBS Gal4-SV40 | Tyr-m-fos-CycA-VP16-m-jun | 31.8 ± 7.8 | 0.8 ± 0.4 |

For standard deviation n = 5

TABLE 6

Percentage of surviving transfected cells in MeWo and H322 cells. All cells were cotransfected using 1 ng of CMV-luc as a marker of the transfected cells.

| Transfected plasmid | | | |
| --- | --- | --- | --- |
| Promoter (reacting to activator) for the expression of Bax cDNA | Activator subunits in pGL3 | % of surviving transfected cell | |
| | | MeWo | H322 |
| CMV | Tyr-m-fos-CycA-VP16 | 9 | 36 |
| CMV | Tyr-m-fos-CycA-VP16-m-jun | 9.5 | 32 |
| 10 x BS Gal4-SV40 | Tyr-m-fos-CycA-VP16 | 100 | 100 |
| 10 x BS Gal4-SV40 | Tyr-m-fos-CycA-VP16-m-jun 36 | 36 | 100 |

TABLE 7

Selective gene expression in melanomas after adenovirus transfer

| Virus used for the infection | | Luciferase activity (RLU) | |
| --- | --- | --- | --- |
| Promotor (reacting | Activator subunits in | MeWo | H322 |
| AdSV40-luc | – | 2692 | 1733 |
| Ad10xBS Gal4-SV40-luc | ADTyr-m-fos- CycA-VP16 | 1053 | 563 |
| Ad10xBS Gal4- SV 40-luc | AdTyr-m-fos-CycA-VP16-m-jun | 186217 | 475 |

Federal Republic of Germany Application 19900743.8, filed Jan. 12, 1999, is hereby incorporated by reference in its entirety.

---

What is claimed is:

1. A complex comprising the following components:
 a) at least one ligand specific for a target structure;
 b) at least one protein comprising a mutated dimerization domain obtained by mutation of a naturally occurring dimerization domain, wherein said mutated dimerization domain binds specifically with component c) and said component b) is covalently bonded to said component a);
 c) at least one protein comprising a mutated dimerization domain obtained by mutation of a naturally occurring dimerization domain, wherein said mutated dimerization domain binds specifically with said component b) and said component c) is covalently bonded to component d); and
 d) at least one effector;
 wherein said components b) and c) are not naturally occurring proteins, and
 wherein said components b) and c) are mutated binding domains of c-fos and c-jun, comprising the following mutations:
  c-fos amino acid 167E→K
  172E→K
  181E→K
  cjun amino acid 283K→E
  288K→E
  302K→E.

2. The complex as claimed in claim 1, wherein said component a) is replaced by said component d).

3. The complex as claimed in claim 1, wherein said component d) is replaced by said component a).

4. The complex as claimed in claim 1, which further comprises a fusogenic peptide or a translocalization peptide.

5. The complex as claimed in claim 1, which further comprises a cleavage sequence for a protease between said components c) and d) or a) and b).

6. The complex as claimed in claim 1, wherein said component a) is selected from the group consisting of: a growth factor, a cytokine, TNF, a chemokine, a peptide hormone, a mediator, a steroid hormone, a vitamin, a complement factor, a clotting factor, a kinin system factor, a fibrinolysis system factor, a plasmatic enzyme, a cell enzyme, a plasmatic enzyme inhibitor, a cell enzyme inhibitor, a virus coat protein, a cell receptor for the afore-mentioned molecules, an antibody, an antibody cleavage produce, a DNA binding protein, a DNA binding domain of a transcription factor and an activation domain of a transcription factor.

7. The complex as claimed in claim 1, wherein said component d) is selected from the group consisting of: inhibitors of cell proliferation, apoptosis-inducing proteins, cytostatic proteins, cytotoxic proteins, coagulation-inducing factors, angiogenesis-inducing factors, angiogenesis-inhibiting factors, growth factors, cytokines, chemokines, interleukins, interferons, complement factors, clotting factors, fibrinolysis-inducing proteins, peptide hormones, mediators, bacterial proteins, receptors, viral antigens, parasitic antigens, tumor antigens, autoantigens, tissue antigens, adhesion molecules, antibodies, antibody cleavage products, enzymes for reacting with a signal-emitting component, enzymes for converting a precursor of an active substance into an active substance, fluorescent dyes, isotopes, metal-binding proteins, and a DNA-binding domain.

8. The complex as claimed in claim 6, wherein said antibody cleavage product is selected from the group consisting of: F(ab)$_2$, a single-chain Fv, a single-chain, a double antigen-binding molecule, and an Fc fragment.

9. The complex as claimed in claim 7, wherein said receptor is selected from the group consisting of receptors for: growth factors, cytokines, chemokines, interleukins, interferons, complement factors, clotting factors, fibrinolysis-inducing proteins, peptide hormones, steroid hormones, mediators, and virus coat proteins.

10. The complex as claimed in claim 7, wherein said antibody cleavage product is selected from the group consisting of: F(ab)$_2$, Fab, single-chain Fv, and single-chain double antigen-binding proteins.

11. The complex as claimed in claim 1, wherein at least one protein of component b) binds specifically with at least one protein of component c) with a binding constant of at least a $K_M$ of $10^{-7}$ mol l$^{-1}$.

12. A vaccine comprising the complex as claimed in claim 1.

\* \* \* \* \*